US012661377B2

(12) United States Patent
Gupta et al.

(10) Patent No.: US 12,661,377 B2
(45) Date of Patent: Jun. 23, 2026

(54) COMBINATION THERAPY COMPRISING A COMPOSITION OF MESENCHYMAL STROMAL CELLS AND HYALURONIC ACID FOR USE IN TREATMENT OF OSTEOARTHRITIS

(71) Applicant: STEMPEUTICS RESEARCH PRIVATE LIMITED, Bengaluru (IN)

(72) Inventors: Pawan Kumar Gupta, Bengaluru (IN); Udaykumar Kolkundkar, Bengaluru (IN); Shivashankar Parashuram, Bengaluru (IN); Suresh Kannan Subramanian Shanmugam, Bengaluru (IN)

(73) Assignee: STEMPEUTICS RESEARCH PRIVATE LIMITED, Karnataka (IN)

( * ) Notice: Subject to any disclaimer, the term of this patent is extended or adjusted under 35 U.S.C. 154(b) by 706 days.

(21) Appl. No.: 18/147,269

(22) Filed: Dec. 28, 2022

(65) Prior Publication Data

US 2024/0189359 A1     Jun. 13, 2024

(30) Foreign Application Priority Data

Dec. 7, 2022     (IN) ............................. 202241070687

(51) Int. Cl.
| | |
|---|---|
| *A61K 35/28* | (2015.01) |
| *A61K 31/728* | (2006.01) |
| *A61P 19/02* | (2006.01) |

(52) U.S. Cl.
CPC ............ *A61K 35/28* (2013.01); *A61K 31/728* (2013.01); *A61P 19/02* (2018.01)

(58) Field of Classification Search
CPC ........ A61K 35/28; A61K 31/728; A61P 19/02
See application file for complete search history.

(56) References Cited

U.S. PATENT DOCUMENTS

2016/0184364 A1     6/2016   Gupta et al.

OTHER PUBLICATIONS

Thej et al. The Role of Mesenchymal Stromal Cells in the Management of Osteoarthritis of the Knee. Update on Mesenchymal and Induced Pluripotent Stem Cells; Edited by Khalid Ahmed Al-Anazi, Intechopen. p. 1-34 (Year: 2019).*

* cited by examiner

*Primary Examiner* — Taeyoon Kim
(74) *Attorney, Agent, or Firm* — Oliff PLC

(57)     ABSTRACT

The present disclosure relates to an ultrasound guided intraarticular administration of a combination of a composition comprising pooled mesenchymal stromal cells, and mid molecular weight hyaluronic acid for treatment of osteoarthritis. The disclosure also provides methods for increasing levels of anti-inflammatory marker and decreasing levels of disease progression marker in a human subject suffering from osteoarthritis through the use of the said combination. The present disclosure accordingly also relates to a kit comprising the said composition and the hyaluronic acid as such for the said use and treatment.

17 Claims, 6 Drawing Sheets

TSP2 SECRETION

PGE2 SECRETION

Figure 1A:
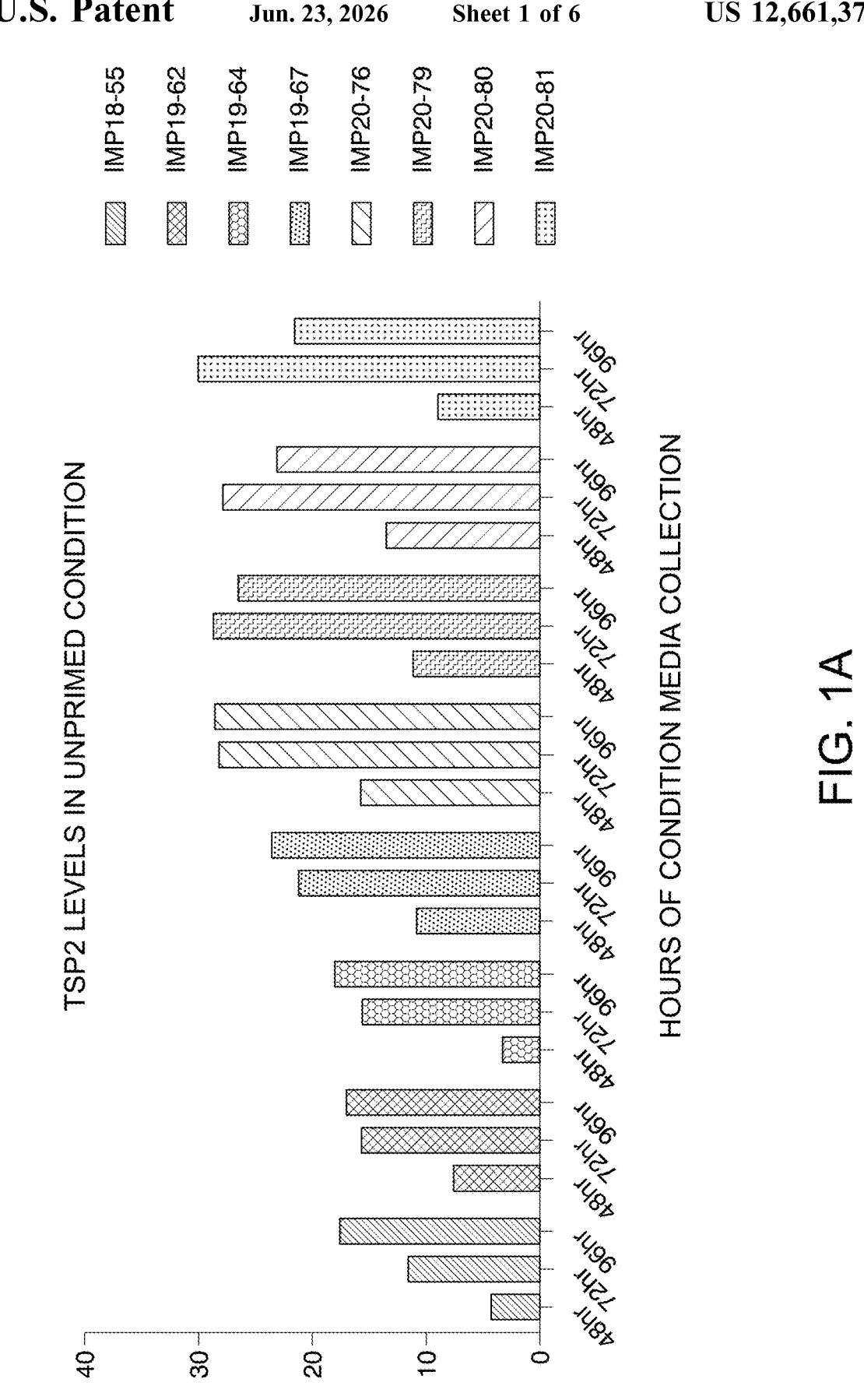

COMBINATION THERAPY COMPRISING A COMPOSITION OF MESENCHYMAL STROMAL CELLS AND HYALURONIC ACID FOR USE IN TREATMENT OF OSTEOARTHRITIS

TECHNICAL FIELD

The present disclosure relates to the field of combination therapy for treatment of osteoarthritis. More particularly, the disclosure relates to an ultrasound guided intraarticular administration of a combination of a composition comprising pooled mesenchymal stromal cells, and mid molecular weight hyaluronic acid for treatment of osteoarthritis. The disclosure also provides methods for increasing levels of anti-inflammatory marker and decreasing levels of disease progression marker in a human subject suffering from osteoarthritis through the use of the said combination. The present disclosure accordingly also relates to a kit comprising the said composition and the hyaluronic acid as such for the said use and treatment.

BACKGROUND OF THE DISCLOSURE

Osteoarthritis (OA) is a degenerative joint disease that can affect many tissues of a joint. Historically, osteoarthritis was known as a "wear and tear" condition, generally associated with aging. But we know now that it is a disease of the entire joint, including bone, cartilage, ligaments, fat and the tissues lining the joint (the synovium).

Symptoms of OA often develop slowly and worsen over time, and include pain, stiffness, tenderness, loss of flexibility, grating sensation, bone spurs and swelling.

There is currently no cure for OA, but medication, assistive devices and other therapies that don't involve drugs can help to ease pain. As a last resort, a damaged joint may be surgically fused or replaced with one made of a combination of metal, plastic and/or ceramic.

Accordingly, the current OA treatments are centered around symptom management. The type of treatment that will help the most largely depends on the severity of the symptoms and their location. Mild cases of OA can be treated with a combination of non-pharmacologic (for example, physiotherapy) and pharmacologic agents to reduce pain and inflammation. However, as the disease progresses, additional aggressive treatments are required. The most common agents employed for the treatment of OA include analgesics, nonsteroidal anti-inflammatory drugs (NSAIDs) such as aspirin, ibuprofen, naproxen and celecoxib, counterirritants such as products containing capsaicin, menthol and lidocaine, corticosteroids and platelet-rich plasma (PRP) therapy.

Although some patients experience temporary relief, the efficacy of these interventions is not uniform and there is significant debate about their effectiveness. In more advanced or severe cases of OA, surgical replacements are the only viable therapeutic option. Hence, the current treatments of OA are only aimed at reducing pain, maintaining mobility, and minimizing disability. None of these approaches however actually cause significant regeneration of the damaged cartilage or provide long term relief that does not require regular therapeutic intervention. The present disclosure provides compositions and methods that aim to solve this unmet need.

SUMMARY OF THE DISCLOSURE

The present disclosure relates to a method of treating osteoarthritis in a human subject, said method comprising administering to the subject a combination of:

a composition comprising about 20 to 30 million mesenchymal stromal cells, multiple electrolyte solution and protein free, serum free, animal component free formulation of dimethyl sulfoxide (DMSO); and
mid molecular weight hyaluronic acid.

In some embodiments of the present disclosure, the composition is devoid of human serum albumin (HSA); and the mesenchymal stromal cells are bone marrow derived pooled mesenchymal stromal cells obtained from pooling mesenchymal stromal cells from at least 3 donors.

In some embodiments of the present disclosure, the composition comprises about 20 to 30 million mesenchymal stromal cells, about 1 ml of multiple electrolyte solution and about 1 ml of protein free, serum free, animal component free formulation of about 2.5% to 5% dimethyl sulfoxide (DMSO).

In some embodiments of the present disclosure, the administration of the composition or the hyaluronic acid or both, is an ultrasound guided administration, through an intra-articular route.

In some embodiments of the present disclosure, the combination provides improvement to the subject in osteoarthritic symptoms selected from a group comprising pain and stiffness; and improves or maintains quality parameters of respective cartilage in the subject, in relation to the subject prior to the administration of the said combination.

The present disclosure also relates to a combination product or a kit comprising the combination as described above.

In some embodiments of the present disclosure, the combination product or the kit comprises the composition as described above along with about 2 ml of hyaluronic acid.

In some embodiments of the present disclosure, the combination as described above is employed for use in a method of treating osteoarthritis in a human subject.

In some embodiments of the present disclosure, the combination as described above is employed for use in a method of increasing levels of anti-inflammatory marker interleukin-10 (IL-10) and/or decreasing levels of disease progression marker crosslinked C-telopeptides of type II collagen (CTX-II) in a human subject suffering from osteoarthritis.

Accordingly, the present disclosure also relates to a method of increasing levels of anti-inflammatory marker interleukin-10 (IL-10) and/or decreasing levels of disease progression marker crosslinked C-telopeptides of type II collagen (CTX-II) in a human subject suffering from osteoarthritis, said method comprising administering to the subject the combination as defined above.

In some embodiments of the present disclosure, the levels of markers are increased and/or decreased in relation to the subject prior to administration of the said combination.

In some embodiments of the present disclosure, the administration of the composition or the hyaluronic acid or both, is an ultrasound guided administration, through an intra-articular route.

BRIEF DESCRIPTION OF THE ACCOMPANYING FIGURES

Figure 1B:
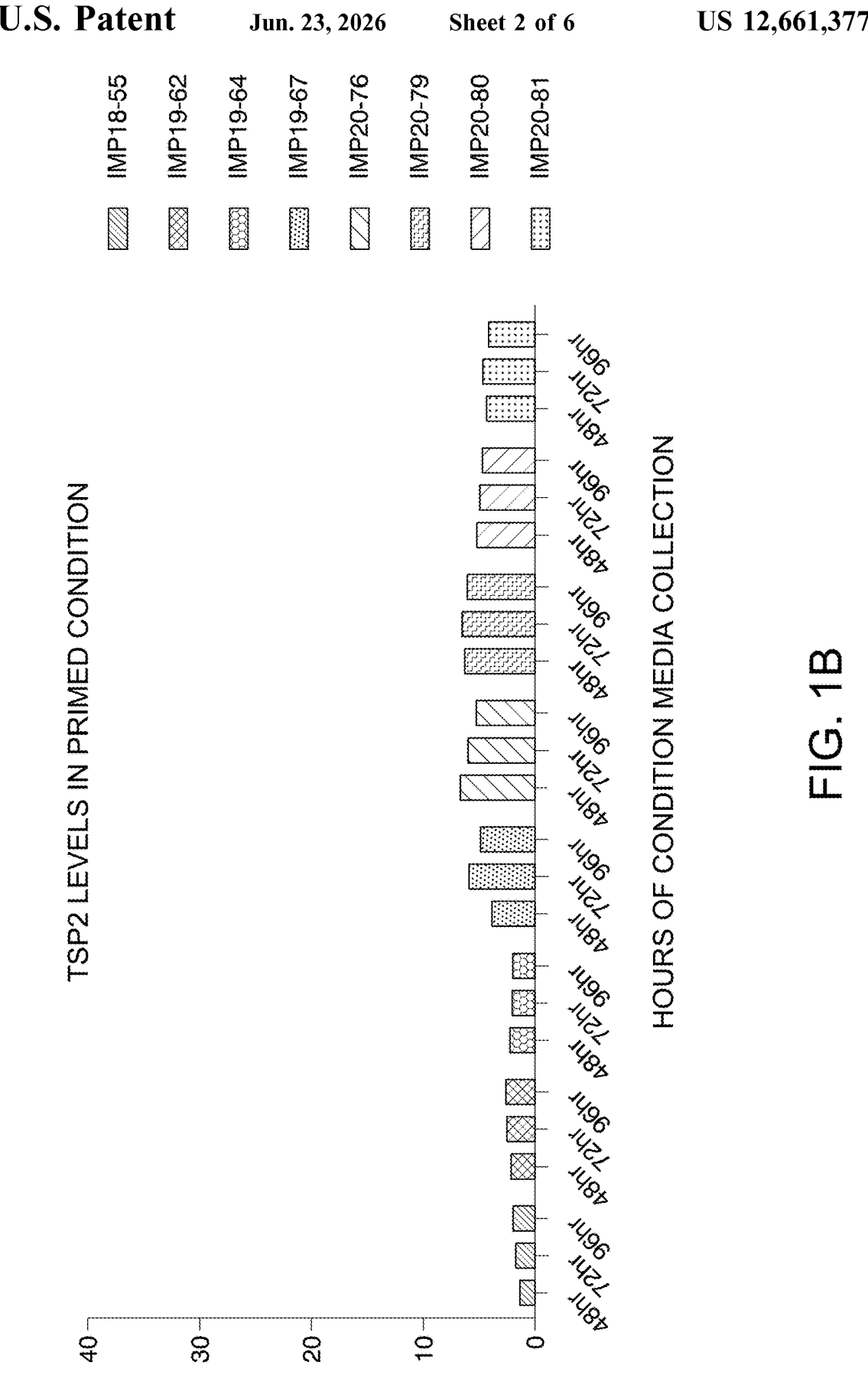

In order that the present disclosure may be readily understood and put into practical effect, reference will now be made to exemplary embodiments as illustrated with reference to the accompanying figures. The figures together with the detailed description below, are incorporated in and form part of the specification, and serve to further illustrate the embodiments and explain various principles and advantages, where:

FIGS. 1A and 1B respectively show TSP-2 secretion levels of unprimed Stempeucel® (in absence of IFN-γ and TNF-α) and primed Stempeucel® (in presence of IFN-γ and TNF-α).

Figure 2A:
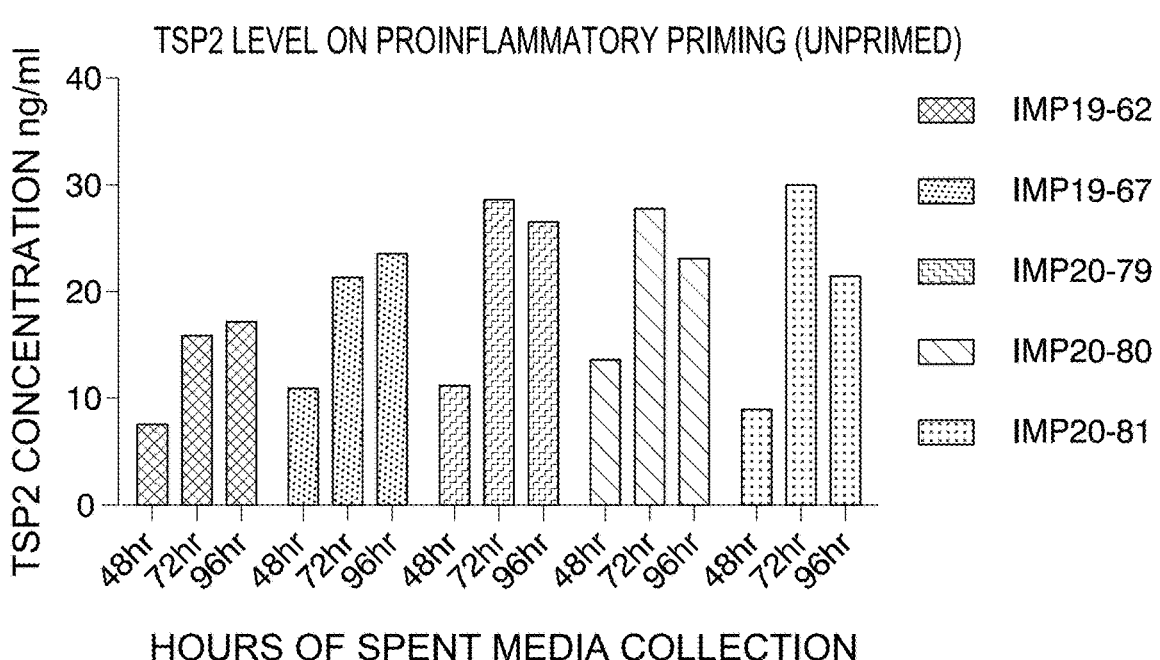
Figure 2A:
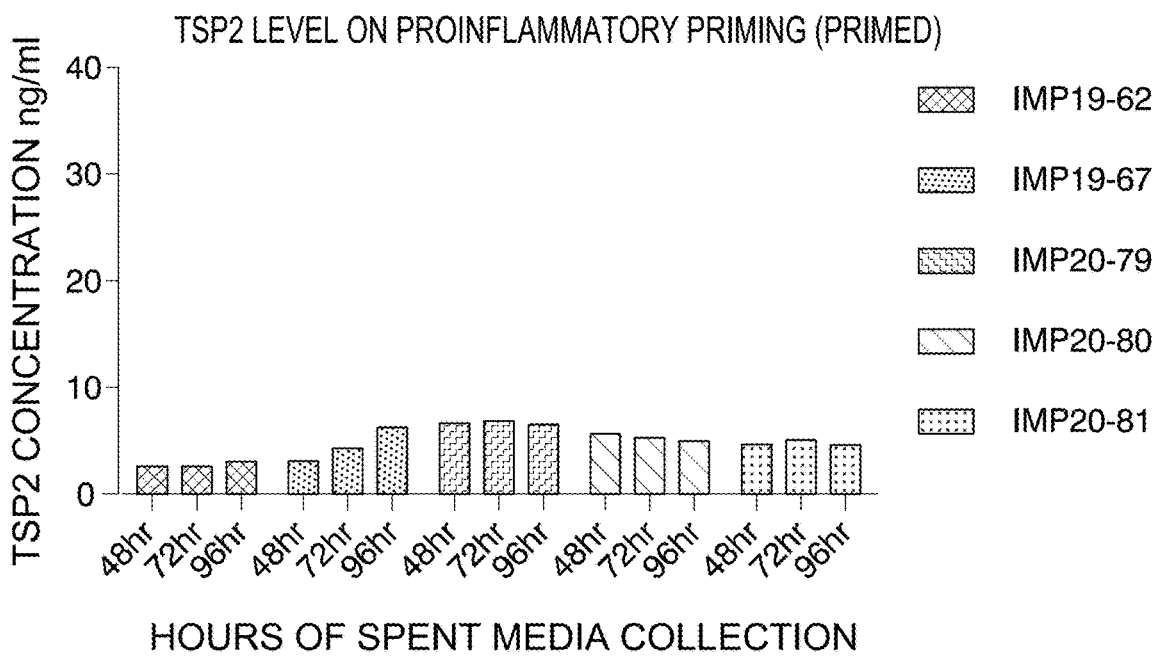
Figure 2B:
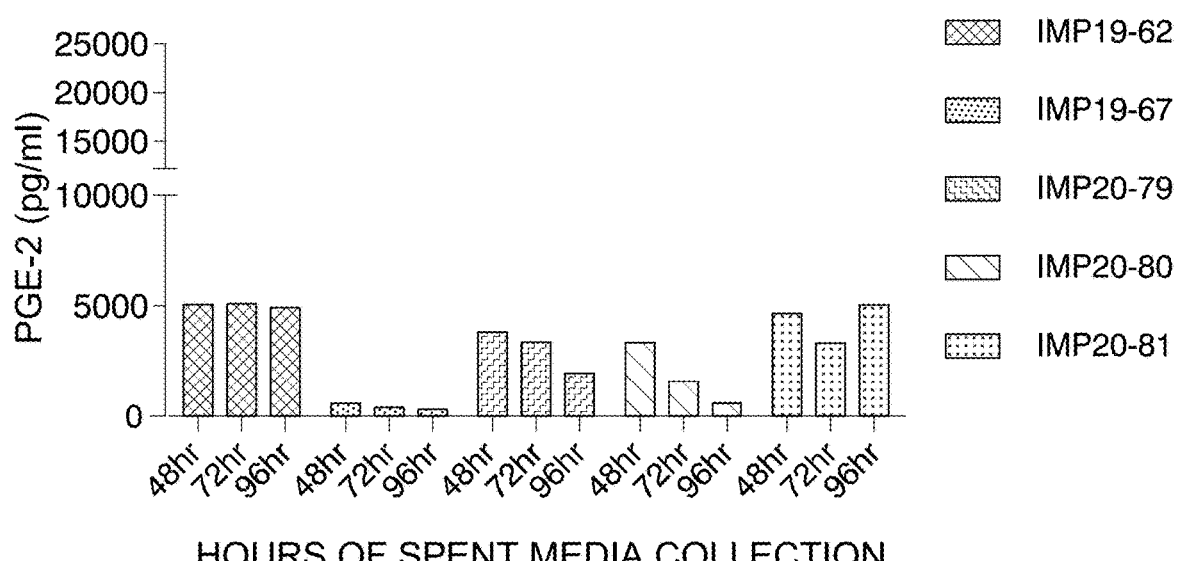
Figure 2B:
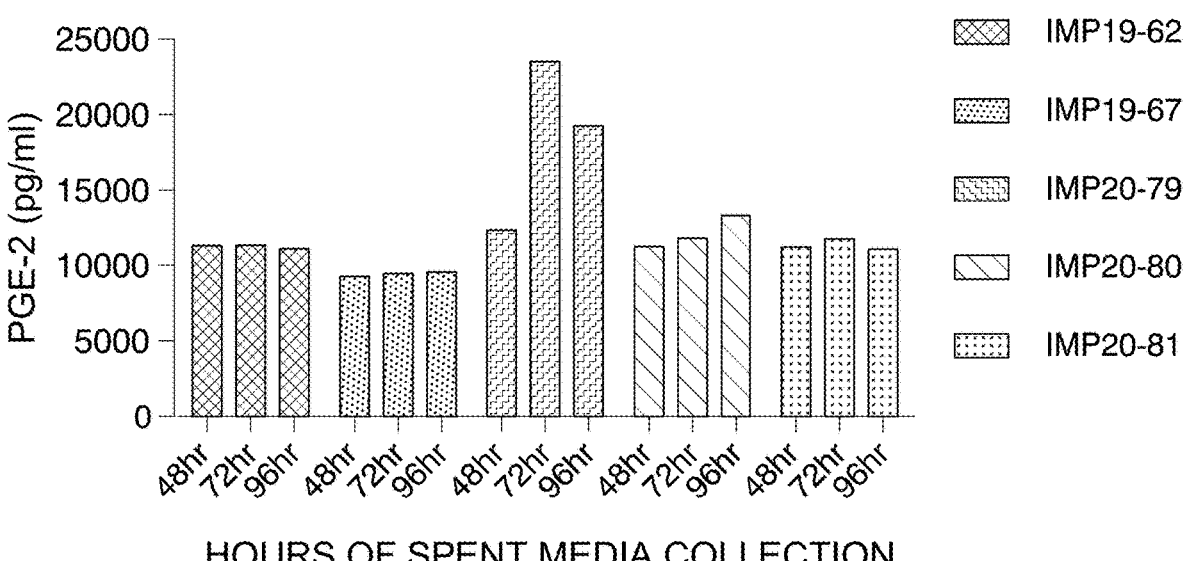
Figure 2C:
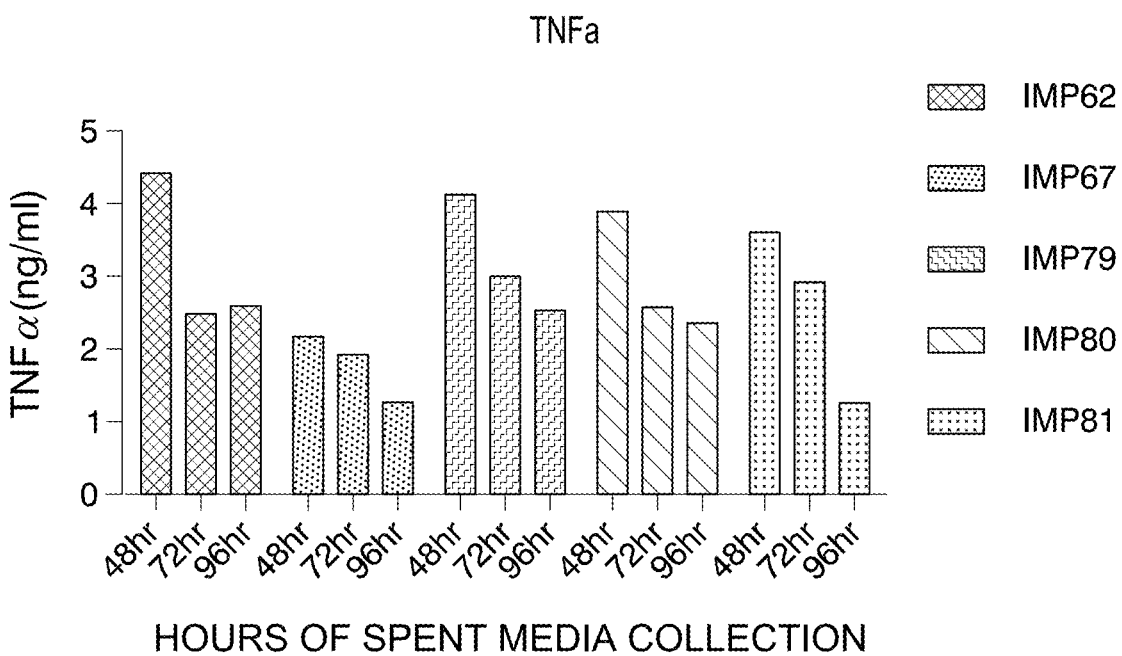

FIGS. 2A, 2B, and 2C respectively show TSP-2 and PGE-2 secretion levels in primed (in presence of IFN-7 and TNF-α) condition; and TSP-2 and PGE-2 secretion levels in unprimed condition; and TNF-α levels in the primed samples.

Figure 3:
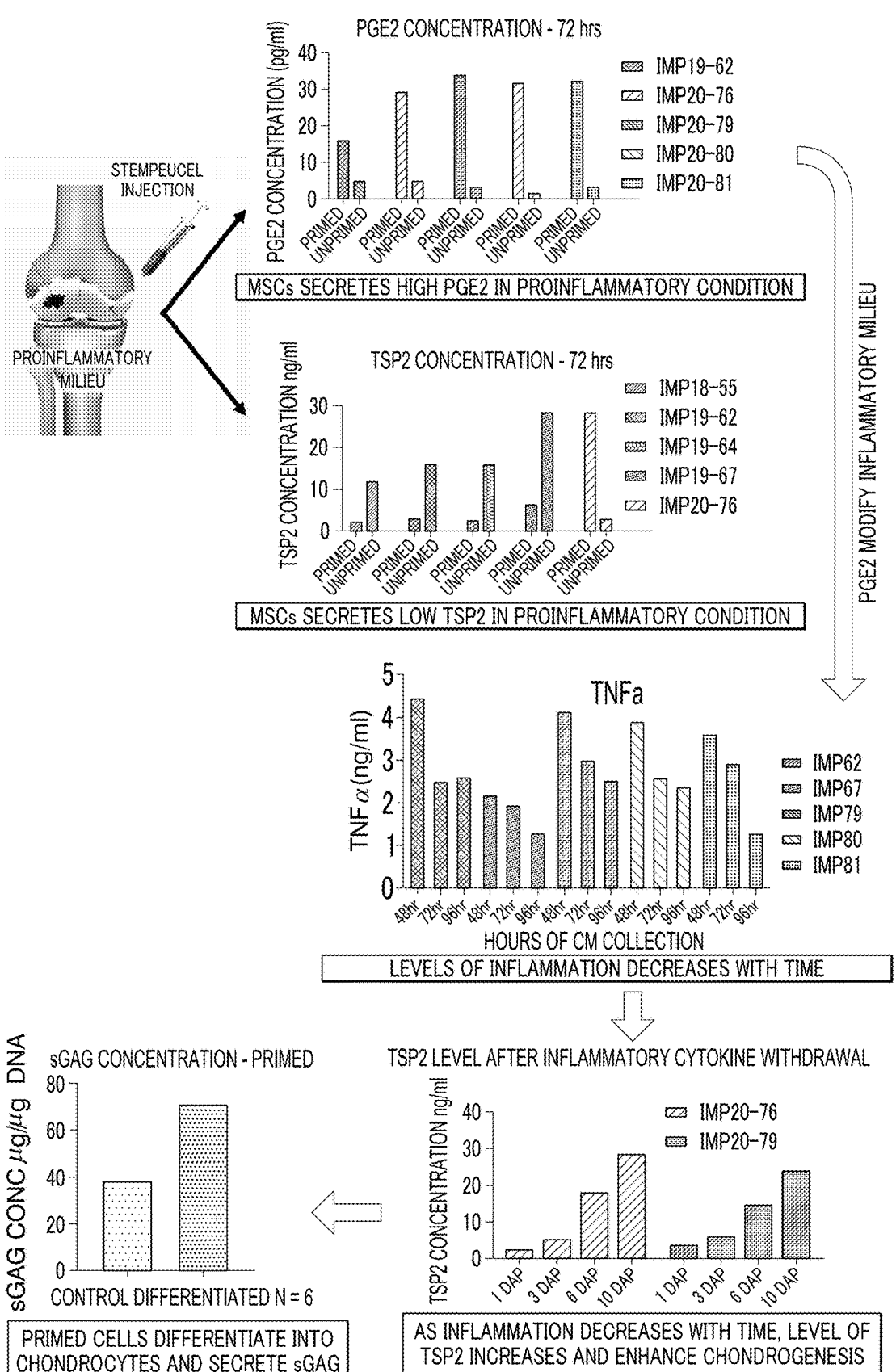

FIG. 3 shows the relevance of TSP-2 as a potential indicator for determining the potency of Stempeucel® for OA indication.

DESCRIPTION OF THE DISCLOSURE

Unless otherwise defined, all terms used in the disclosure, including technical and scientific terms, have meaning as commonly understood by one of ordinary skill in the art to which this invention belongs. By means of further guidance, definitions for some terms are included for better understanding of the present disclosure.

As used herein, the singular forms 'a', 'an' and 'the' include both singular and plural referents unless the context clearly dictates otherwise.

The term 'comprising', 'comprises' or 'comprised of' as used herein are synonymous with 'including', 'includes', 'containing' or 'contains' and are inclusive or open-ended and do not exclude additional, non-recited members, elements or method steps.

The recitation of numerical ranges by endpoints includes all numbers and fractions subsumed within the respective ranges, as well as the recited endpoints.

The term 'about' as used herein when referring to a measurable value such as a parameter, an amount, a temporal duration, and the like, is meant to encompass variations of +10% or less, preferably +5% or less, more preferably +1% or less and still more preferably +0.1% or less of and from the specified value, insofar such variations are appropriate to perform the present disclosure. It is to be understood that the value to which the modifier 'about' refers is itself also specifically, and preferably disclosed.

As used herein, the term 'treating' or 'treatment' or the likes, used with respect to the disease osteoarthritis within the present disclosure is meant to refer to the ordinary meaning of the term known to a person skilled in the art. The term is broadly employed in the present disclosure to refer to management of osteoarthritis after it has been diagnosed, to allow partial or complete relief to a patient suffering from one or more of the symptoms commonly associated with it. The term is also used to refer to a medical regimen that allows for cure, elimination or reduction in the levels of osteoarthritis or clinical/biological markers associated therewith, or to a medical regimen that slows progression of the disease as such. While a person skilled in the art understands the modes and mechanisms to ascertain whether a regimen is leading to a successful treatment or not, an example of such a mechanism is to compare the percentage change of a symptom from the baseline value before and after administration of a treatment regimen.

In order to meet the need of the art for patients suffering from osteoarthritis (OA), and to plug the gaps existing in the current lines of treatment for such patients, the present disclosure provides a combination therapy for treating osteoarthritis in a human subject, said method comprising administering to the subject a combination of:

a composition comprising about 20 to 30 million mesenchymal stromal cells, multiple electrolyte solution and protein free, serum free, animal component free formulation of dimethyl sulfoxide (DMSO); and mid molecular weight hyaluronic acid.

In some embodiments, the composition employed as part of the combination therapy of the present disclosure is devoid of human serum albumin (HSA).

In some embodiments, the mesenchymal stromal cells that form the core component of the composition of the present disclosure are bone marrow derived pooled mesenchymal cells obtained from pooling mesenchymal stromal cells from at least 3 donors.

In some embodiments, the administration of the composition or the hyaluronic acid or both, as part of the combination therapy of the present disclosure is an ultrasound guided administration, through an intra-articular route.

Thus, more particularly, the present disclosure provides a method of treating osteoarthritis in a human subject, said method comprising administering to the subject a combination of:

a composition comprising about 20 to 30 million mesenchymal stromal cells, multiple electrolyte solution and protein free, serum free, animal component free formulation of dimethyl sulfoxide (DMSO); and mid molecular weight hyaluronic acid, wherein the composition is devoid of human serum albumin (HSA); wherein the mesenchymal stromal cells are bone marrow derived pooled mesenchymal cells obtained from pooling mesenchymal stromal cells from at least 3 donors; and wherein the administration of the composition or the hyaluronic acid or both, is an ultrasound guided administration, through an intra-articular route.

In some embodiments, the osteoarthritis being treated through the combination therapy of the present disclosure is a Grade II or Grade III osteoarthritis.

In some embodiments, the said composition comprises about 25 million pooled mesenchymal stromal cells.

In some embodiments, the multiple electrolyte solution present within the composition of the combination therapy of the present disclosure is Plasmalyte A.

In some embodiments, the multiple electrolyte solution is present within the composition of the combination therapy of the present disclosure at an amount of about 1 ml.

In some embodiments, the DMSO is present within the composition of the combination therapy of the present disclosure at an amount of about 1 ml.

In some embodiments, the DMSO is present within the composition of the combination therapy of the present disclosure as a solution having a concentration of about 2.5%.

In some embodiments, the DMSO is present within the composition of the combination therapy of the present disclosure as a solution having a concentration of about 5%.

Accordingly, in some embodiments, the combination therapy of the present disclosure comprises administering a composition comprising about 20 to 30 million mesenchymal stromal cells, about 1 ml of multiple electrolyte solution and about 1 ml of protein free, serum free, animal component free formulation of about 2.5% to 5% dimethyl sulfoxide (DMSO); and about 2 ml of hyaluronic acid, wherein the composition is devoid of human serum albumin (HSA).

In some embodiments, the combination therapy of the present disclosure comprises administering a composition consisting of about 20 to 30 million mesenchymal stromal cells, about 1 ml of multiple electrolyte solution and about 1 ml of protein free, serum free, animal component free formulation of about 2.5% to 5% dimethyl sulfoxide (DMSO); and about 2 ml of hyaluronic acid, wherein the composition is devoid of human serum albumin (HSA).

Accordingly, in some embodiments, the combination therapy of the present disclosure comprises administering a composition comprising about 25 million mesenchymal stromal cells, about 1 ml of multiple electrolyte solution and about 1 ml of protein free, serum free, animal component free formulation of about 2.5% to 5% dimethyl sulfoxide (DMSO); and about 2 ml of hyaluronic acid, wherein the composition is devoid of human serum albumin (HSA).

In some embodiments, the combination therapy of the present disclosure comprises administering a composition consisting of about 25 million mesenchymal stromal cells, about 1 ml of multiple electrolyte solution and about 1 ml of protein free, serum free, animal component free formulation of about 2.5% to 5% dimethyl sulfoxide (DMSO); and about 2 ml of hyaluronic acid, wherein the composition is devoid of human serum albumin (HSA).

In some embodiments, the combination therapy of the present disclosure comprises administering a composition consisting of about 25 million mesenchymal stromal cells, about 1 ml of multiple electrolyte solution and about 1 ml of protein free, serum free, animal component free formulation of about 2.5% dimethyl sulfoxide (DMSO); and about 2 ml of hyaluronic acid, wherein the composition is devoid of human serum albumin (HSA).

In some embodiments, the combination therapy of the present disclosure comprises administering a composition consisting of about 25 million mesenchymal stromal cells, about 1 ml of multiple electrolyte solution and about 1 ml of protein free, serum free, animal component free formulation of about 5% dimethyl sulfoxide (DMSO); and about 2 ml of hyaluronic acid, wherein the composition is devoid of human serum albumin (HSA).

In some embodiments, it is the composition that is administered through a single dose intra-articular administration. Alternatively, in some embodiments, it is the hyaluronic acid that is administered through a single dose intra-articular administration.

Accordingly, in case where only one of the composition or the hyaluronic acid is administered through an ultrasound guided intra-articular administration, the other component is administered through a conventional single dose intra-articular administration.

In some embodiments, both, the composition as well as the hyaluronic acid are administered through an ultrasound guided intra-articular administration.

In some embodiments, both, the composition as well as the hyaluronic acid are administered through an ultrasound guided intra-articular administration, injected one after the other with the same needle.

Ultrasound guided administration is a non-invasive, portable, radiation-free administration and provides dynamic evaluation. Some of its advantages are:

real-time visualization, helps in effective pre-procedure planning, helps to reduce complications, and less time spent during the administration.

In some embodiments, the ultrasound guided administration resulted in better accuracy than anatomical guidance (95.8% versus 77.8%, P<0.001), yielding an odds ratio of 6.4 (95% confidence interval 2.9-14). Accordingly, the ultrasound guidance notably improves injection accuracy in the target intra-articular joint space of large joints including the knee.

Nonetheless, regardless of how the composition and the hyaluronic acid are administered, the administration continues to be a single dose administration for both the composition and the hyaluronic acid, and no repetition of dose is required for up to a period of about 6 months from the first dose. Accordingly, a single dose administration of the composition and the hyaluronic acid continues to be sufficient for up to about 6 months for treating osteoarthritis as per the present disclosure.

In some embodiments, no repetition of dose is required for up to a period of about 12 months from the first dose. Accordingly, a single dose administration of the composition and the hyaluronic acid continues to be sufficient for up to about 12 months for treating osteoarthritis as per the present disclosure. In some embodiments, the composition and the hyaluronic acid are administered simultaneously as part of the combination therapy of the present disclosure.

In some embodiments, the composition and the hyaluronic acid are administered sequentially as part of the combination therapy of the present disclosure. In such a case, the administration of the hyaluronic acid could follow or lead the administration of the composition.

In some embodiments, when the composition and the hyaluronic acid are administered sequentially as part of the combination therapy of the present disclosure, the hyaluronic acid is administered immediately after the administration of the composition.

In some embodiments, when the composition and the hyaluronic acid are administered sequentially as part of the combination therapy of the present disclosure, the hyaluronic acid is administered post about 1 second to about 30 minutes of the administration of the composition or within 1800 seconds of the administration of the composition.

In some embodiments, when the composition and the hyaluronic acid are administered sequentially as part of the combination therapy of the present disclosure, the hyaluronic acid is administered within 60 seconds of the administration of the composition.

In some embodiments, when the composition and the hyaluronic acid are administered sequentially as part of the combination therapy of the present disclosure, the hyaluronic acid is administered within 30 seconds of the administration of the composition.

In some embodiments, when the composition and the hyaluronic acid are administered sequentially as part of the combination therapy of the present disclosure, the hyaluronic acid is administered within 10 seconds of the administration of the composition.

In some embodiments, the amount of hyaluronic acid administered as part of the combination therapy of the present disclosure is about 2 ml.

In some embodiments, the hyaluronic acid administered comprises 20 mg of hyaluronic acid administered in 2 ml of buffered physiological sodium chloride having pH of 6.8 to 7.5.

The combination therapy of the present disclosure provides improvement to the subject in osteoarthritic symptoms selected from a group comprising pain and stiffness; and improves or maintains quality parameters of respective cartilage in the subject, in relation to the subject prior to the administration of the said combination.

In some embodiments, the quality parameters of the cartilage are selected from a group comprising quality of articular cartilage such as areas of altered composition and ultrastructure, cartilage thickness, cartilage morphology and cartilage volume.

In some embodiments, the improvement in one or more osteoarthritic symptom is measured by comparing the change in the baseline value of a subject from before and after the treatment with the combination therapy of the present disclosure.

In some embodiments, the improvement in one or more osteoarthritic symptom is measured by comparing the change in the baseline value of a subject treated with the combination therapy of the present disclosure, with another subject having an identical or similar level of disease but not treated with the combination therapy of the present disclosure.

In some embodiments, the osteoarthritic symptom improved by the combination therapy of the present disclosure is measured through a score selected from a group comprising WOMAC composite index score, WOMAC pain index score, WOMAC stiffness index score, WOMAC physical function index score and VAS score, or any combination thereof. As is well understood in the field of osteoarthritis, the WOMAC or the The Western Ontario and McMaster Universities Osteoarthritis Index scores are widely used proprietary set of standardized questionnaires used by health professionals to evaluate the condition of patients with osteoarthritis of the knee and hip, including pain, stiffness, and physical functioning of the joints.

Accordingly, in some embodiments, the osteoarthritic symptom improved by the combination therapy of the present disclosure is measured through a WOMAC composite index score.

In some embodiments, the combination therapy of the present disclosure improves mean percentage change from baseline in a WOMAC composite index score by about 26% in a span of about 6 months.

In some embodiments, the combination therapy of the present disclosure shows a mean difference in percentage change from baseline for a WOMAC composite index score by at least about 20% at the 6 months timepoint.

In some embodiments, the combination therapy of the present disclosure shows a mean difference in percentage change from baseline for a WOMAC composite index score by about 23% at the 6 months timepoint.

In some embodiments, the combination therapy of the present disclosure shows a mean difference in percentage change from baseline for a WOMAC composite index score by at least about 40% at the 12 months timepoint.

In some embodiments, the combination therapy of the present disclosure shows a mean difference in percentage change from baseline for a WOMAC composite index score by about 45% at the 12 months timepoint.

Similarly, in some embodiments, the osteoarthritic symptom improved by the combination therapy of the present disclosure is measured through a WOMAC pain index score.

In some embodiments, the combination therapy of the present disclosure improves mean percentage change from baseline in a WOMAC pain index score by about 27% in a span of about 6 months.

In some embodiments, the combination therapy of the present disclosure shows a mean difference in percentage change from baseline for a WOMAC pain index score by at least about 20% at the 6 months timepoint.

In some embodiments, the combination therapy of the present disclosure shows a mean difference in percentage change from baseline for a WOMAC pain index score by about 26% at the 6 months timepoint.

In some embodiments, the combination therapy of the present disclosure shows a mean difference in percentage change from baseline for a WOMAC pain index score by at least about 40% at the 12 months timepoint.

In some embodiments, the combination therapy of the present disclosure shows a mean difference in percentage change from baseline for a WOMAC pain index score by about 46% at the 12 months timepoint.

Further, in some embodiments, the osteoarthritic symptom improved by the combination therapy of the present disclosure is measured through a WOMAC stiffness index score.

In some embodiments, the combination therapy of the present disclosure improves mean percentage change from baseline in a WOMAC stiffness index score by about 11% in a span of about 6 months.

In some embodiments, the combination therapy of the present disclosure shows a mean difference in percentage change from baseline for a WOMAC stiffness index score by at least about 25% at the 6 months timepoint.

In some embodiments, the combination therapy of the present disclosure shows a mean difference in percentage change from baseline for a WOMAC stiffness index score by about 31% at the 6 months timepoint.

In some embodiments, the combination therapy of the present disclosure shows a mean difference in percentage change from baseline for a WOMAC stiffness index score by at least about 50% at the 12 months timepoint.

In some embodiments, the combination therapy of the present disclosure shows a mean difference in percentage change from baseline for a WOMAC stiffness index score by about 55% at the 12 months timepoint.

Further, in some embodiments, the osteoarthritic symptom improved by the combination therapy of the present disclosure is measured through a WOMAC physical function index score.

In some embodiments, the combination therapy of the present disclosure improves mean percentage change from baseline in a WOMAC physical function index score by about 27% in a span of about 6 months.

In some embodiments, the combination therapy of the present disclosure shows a mean difference in percentage change from baseline for a WOMAC physical function index score by at least about 15% at the 6 months timepoint.

In some embodiments, the combination therapy of the present disclosure shows a mean difference in percentage change from baseline for a WOMAC physical function index score by about 22% at the 6 months timepoint.

In some embodiments, the combination therapy of the present disclosure shows a mean difference in percentage change from baseline for a WOMAC physical function index score by at least about 40% at the 12 months timepoint.

In some embodiments, the combination therapy of the present disclosure shows a mean difference in percentage change from baseline for a WOMAC physical function index score by about 45% at the 12 months timepoint.

Further in some embodiments, the osteoarthritic symptom improved by the combination therapy of the present disclosure is measured through a VAS score.

In some embodiments, the combination therapy of the present disclosure improves mean percentage change from baseline in a VAS score by about 26% in a span of about 6 months.

In some embodiments, the combination therapy of the present disclosure shows a mean difference in percentage change from baseline for a VAS score by at least about 10% at the 6 months timepoint.

In some embodiments, the combination therapy of the present disclosure shows a mean difference in percentage change from baseline for a VAS score by about 17% at the 6 months timepoint.

In some embodiments, the combination therapy of the present disclosure shows a mean difference in percentage change from baseline for a VAS score by at least about 35% at the 12 months timepoint.

In some embodiments, the combination therapy of the present disclosure shows a mean difference in percentage change from baseline for a VAS score by about 41% at the 12 months timepoint.

Thus, in some embodiments, the combination therapy of the present disclosure improves mean percentage change from baseline in a WOMAC composite index score and/or WOMAC pain index score and/or WOMAC stiffness index score and/or WOMAC physical function index score and/or VAS score by at least about 10% in a span of about 6 months.

Similarly, in some embodiments, the combination therapy of the present disclosure shows a mean difference in percentage change from baseline for a WOMAC composite index score and/or WOMAC pain index score and/or WOMAC stiffness index score and/or WOMAC physical function index score and/or VAS score by at least about 15% at the 6 months timepoint.

Likewise, in some embodiments, the combination therapy of the present disclosure shows a mean difference in percentage change from baseline for a WOMAC composite index score and/or WOMAC pain index score and/or WOMAC stiffness index score and/or WOMAC physical function index score and/or VAS score by at least about 40% at the 12 months timepoint.

Accordingly, in some embodiments, the combination therapy of the present disclosure shows a mean difference of the percentage change from baseline (in which the p-value for the mean difference is 0.001 or less) to be (any one or combination of the following):

at least 20.0% at 6 months for WOMAC Composite Index, WOMAC Pain Index, WOMAC Stiffness Index, and/or WOMAC Physical Function Index;

at least 40.0% at 12 months for WOMAC Composite Index, WOMAC Pain Index, WOMAC Stiffness Index, and/or WOMAC Physical Function Index;

at least 35.0% at 12 months for VAS Index and optionally at least 10.0% at 6 months for VAS Index;

at least 25.0% at 6 months for WOMAC Pain Index and/or WOMAC Stiffness Index;

at least 30.0% at 6 months for WOMAC Stiffness Index;

at least 45.0% at 12 months for WOMAC Composite Index, WOMAC Pain Index, WOMAC Stiffness Index, and/or WOMAC Physical Function Index;

at least 50.0% at 12 months for WOMAC Stiffness Index;

at least 55.0% at 12 months for WOMAC Stiffness Index;

at least 40.0% at 12 months for VAS Index and optionally at least 15.0% at 6 months for VAS Index;

from 20.0% to 35.0% at 6 months for WOMAC Composite Index, WOMAC Pain Index, WOMAC Stiffness Index, and/or WOMAC Physical Function Index;

from 20.0% to 30.0% at 6 months for WOMAC Composite Index, WOMAC Pain Index, and/or WOMAC Physical Function Index;

from 40.0% to 60.0% at 12 months for WOMAC Composite Index, WOMAC Pain Index, WOMAC Stiffness Index, and/or WOMAC Physical Function Index;

from 40.0% to 50.0% at 12 months for WOMAC Composite Index, WOMAC Pain Index, and/or WOMAC Physical Function Index; and from 35.0% to 45.0% at 12 months for VAS Index and optionally from 10.0% to 20.0% at 6 months for VAS Index.

In some embodiments, the combination therapy of the present disclosure improves quality parameters of the cartilage selected from a group comprising the quality of articular cartilage such as areas of altered composition and ultrastructure, cartilage thickness, cartilage morphology and cartilage volume.

In some embodiments, the combination therapy of the present disclosure increases levels of anti-inflammatory marker interleukin-10 (IL-10) in a subject, in relation to the subject prior to the administration of the said combination.

In some embodiments, the combination therapy of the present disclosure decreases levels of disease progression marker crosslinked C-telopeptides of type II collagen (CTX-II) in a subject, in relation to the subject prior to the administration of the said combination.

Thus, in some embodiments, the combination therapy of the present disclosure increases levels of anti-inflammatory marker interleukin-10 (IL-10) and decreases levels of disease progression marker crosslinked C-telopeptides of type II collagen (CTX-II) in the subject, in relation to the subject prior to the administration of the said combination.

In some embodiments, the combination therapy of the present disclosure increases levels of anti-inflammatory marker interleukin-10 (IL-10) by about 0.051 pg/mol in a subject over a period of 365 days, when compared to the marker levels in the subject prior to the administration of the said combination. On the other hand, the levels of IL-10 reduced due to disease progression by about 0.228 pg/mol in the subject, in absence of the said combination therapy.

Thus, in some embodiments, for the sake of comparison, if the starting levels of IL-10 are considered to be 0 at day 0, the combination therapy of the present disclosure improved the IL-10 levels by about 5% over a period of 365 days, when compared to reduction in its levels by about 22% in a subject where the combination therapy of the present disclosure was not administered.

In some embodiments, the combination therapy of the present disclosure decreases levels of disease progression marker crosslinked C-telopeptides of type II collagen (CTX-II) by about 44.784 ng/mmol in a subject over a period of 90 days, when compared to the marker levels in the subject prior to the administration of the said combination. On the other hand, the levels of CTX-II increased due to disease progression by about 83.612 ng/mmol in the subject, in absence of the said combination therapy.

Thus, in some embodiments, for the sake of comparison, if the starting levels of CTX-II are considered to be 0 at day 0, the combination therapy of the present disclosure reduced the CTX-II levels by about 44% over a period of 90 days, when compared to increase in its levels by about 83% in a subject where the combination therapy of the present disclosure was not administered.

Without wished to be bound by a specific theory, the expected mechanism of action of the current combination therapy for OA is as follows: The combination of the present disclosure has the potential to secrete various paracrine factors including PGE-2 and TSP-2, which plays a major role as anti-inflammatory and pro chondrogenesis signal, respectively. The combination in the in vitro inflammatory environment in presence of IFN-γ and TNF-α (mimics the proinflammatory milieu in knee joint of OA patients) secreted high levels of PGE-2 and low levels of TSP-2. The secreted PGE-2 from the combination inhibits any further synthesis of pro inflammatory cytokines and modifies the inflammatory milieu. Once the level of pro inflammatory cytokines decrease, the secretion of TSP-2 increases gradually and the TSP-2 is known to stimulate the chondrogenic progenitor cells and promote their differentiation into mature chondrocytes. At the same time, the primed MSCs as part of the combination still retains the potential to differentiate into chondrocytes. Additionally, the hyaluronic acid facilitates the migration and adherence of the MSCs. The hyaluronic acid used along with the MSC composition acts as scaffold and will help in homing of the cells to the site of defect. So, the combination, by both the ways i.e., paracrine action and differentiation into chondrocytes is used as treatment option for OA.

Thus, as will be apparent to a person skilled in the art from a reading of the present disclosure, the criticality of the present disclosure lies in the specificity or selection of the features that results in the combination therapy of the present disclosure. Therefore, the positive effects and improvements that are seen by a human subject suffering from osteoarthritis after undergoing treatment with the combination therapy of the present disclosure is a direct result of amalgamation of features that include:

specific number of pooled mesenchymal stromal cells present in the composition,
   number of donors that form the basis for arriving at the pooled mesenchymal stromal cells,
   presence of multiple electrolyte solution and protein free, serum free, animal component free formulation of dimethyl sulfoxide (DMSO),
   absence of human serum albumin (HSA),
   mid molecular weight of hyaluronic acid, and
   single dose administration of the composition or the hyaluronic acid or both through an ultrasound guided intra-articular route.

Now, in order to facilitate the administration of the combination therapy as described above, the present disclosure accordingly also provides a combination product or a kit as such that comprises the two components employed in the combination therapy.

The present disclosure accordingly also relates to a combination product or a kit for treating osteoarthritis in a human subject, comprising a combination of:

a composition comprising about 20 to 30 million mesenchymal stromal cells, about 1 ml of multiple electrolyte solution and about 1 ml of protein free, serum free, animal component free formulation of about 2.5% to 5% dimethyl sulfoxide (DMSO); and
   about 2 ml of hyaluronic acid, wherein the composition is devoid of human serum albumin (HSA); and wherein the mesenchymal stromal cells are pooled mesenchymal cells obtained from pooling mesenchymal stromal cells from at least 3 donors.

In some embodiments, the amount of hyaluronic acid administered as part of the combination therapy of the present disclosure is about 2 ml.

In some embodiments, the hyaluronic acid administered comprises 20 mg of hyaluronic acid administered in 2 ml of buffered physiological sodium chloride having pH of 6.8 to 7.5.

In some embodiments, the combination product or kit further comprises an instruction manual having instructions on administering the composition and hyaluronic acid, during the course of combination therapy of the present disclosure.

In some embodiments, the composition of the combination therapy, product or kit of the present disclosure comprises about 25 million pooled mesenchymal stromal cells.

Accordingly, in some embodiments, the composition of the combination therapy, product or kit of the present disclosure comprises about 20 million, 21 million, 22 million, 23 million, 24 million, 25 million, 26 million, 27 million, 28 million, 29 million or 30 million pooled mesenchymal stromal cells, including any number of cells therein between.

Thus, the composition of the combination therapy, product or kit of the present disclosure comprises about 25 million mesenchymal stromal cells, about 1 ml of multiple electrolyte solution and about 1 ml of protein free, serum free, animal component free formulation of about 2.5% to 5% dimethyl sulfoxide (DMSO).

Further, the composition of the combination therapy, product or kit of the present disclosure comprises about 25 million mesenchymal stromal cells, about 1 ml of multiple electrolyte solution and about 1 ml of protein free, serum free, animal component free formulation of about 2.5% dimethyl sulfoxide (DMSO).

Furthermore, the composition of the combination therapy, product or kit of the present disclosure comprises about 25 million mesenchymal stromal cells, about 1 ml of multiple electrolyte solution and about 1 ml of protein free, serum free, animal component free formulation of about 5% dimethyl sulfoxide (DMSO).

As will be clear to a person skilled in the art, the terms mesenchymal stromal cells or mesenchymal stem cells are used in interchangeably, and are commonly represented by the abbreviation MSCs within the ambit of the present disclosure.

In some embodiments, the MSCs present in the composition of the combination therapy, product or kit of the present disclosure are bone marrow derived MSCs (BM-MSCs).

Alternatively, the MSCs present in the composition of the combination therapy, product or kit of the present disclosure are derived from a source selected from a group comprising but not limiting to adipose tissue, Wharton's jelly and dental pulp, or any combination thereof.

Thus, the source of MSCs is not a limitation for their presence in the composition of the combination therapy, product or kit of the present disclosure, and a person skilled in the art can employ MSCs derived from any of the sources known to it.

In some embodiments, the MSCs present in the composition of the combination therapy, product or kit of the present disclosure are allogeneic. Allogeneic MSCs refer to MSCs which are derived from individual(s)/donor(s) other than the recipient, however belonging to the same species.

In some embodiments, the MSCs employed as part of the composition herein are derived from bone marrow of multiple healthy donors as per statutory requirement with proper informed consent and approval. Alternatively, the MSCs are bone marrow derived MSCs obtained by ex-vivo culturing or cell banks.

In some embodiments, MSCs employed as part of the composition herein are individually isolated from bone marrows of at least 3 donors, and subjected to various processes to store or cryopreserve said cells. The MSCs employed in the composition herein is pooled from these individual MSCs. Prior to pooling, the MSCs of each individual donor are passaged and cultured to obtain Master Cell Bank composition (MCB). Said MCB comprising MSCs isolated and cultured from individual donors and is cyropreserved in agents such as Fetal Bovine Serum (FBS) and Dimethyl Sulphoxide (DMSO). In some embodiments, the MCB comprises MSCs of individual donors, cyropreserved in FBS at a concentration of about 90% and DMSO at a concentration of about 10%. The MSCs are thereafter pooled to prepare the cell composition which is employed in the combination therapy, product or kit of the present disclosure. Pooling can be defined as combining/mixing of MSCs of at least three donors from MCB in manufacturing process. The pooled MSCs are subsequently passaged to arrive at a Working Cell Bank composition (WCB). The WCB therefore comprises pooled MSCs, which is further subjected to passaging/culturing, and washing process to remove presence of xeno or other impurities to obtain a final composition or the investigational medicinal product (IMP) comprising pooled allogeneic MSCs for employing as part of the combination therapy, product or kit in the present disclosure.

The MSCs so obtained are accordingly mixed with about 1 ml of multiple electrolyte solution, which is plasmalyte A and about 1 ml of protein free, serum free, animal component free formulation of about 2.5% to 5% dimethyl sulfoxide (DMSO), to obtain the composition employed in the present disclosure.

In some embodiments, the 5% dimethyl sulfoxide (DMSO) employed as part of the composition herein is commercially available CryoStor5 (CS5).

In some embodiments, a person skilled in the art would understand that the DMSO is generally employed to cryopreserve a formulation or composition of mesenchymal stromal cells, such as the one employed in the present disclosure. Accordingly, the DMSO need not be mandatorily included within the composition of the present disclosure, if the preparation of the mesenchymal stromal cells is being freshly prepared for administration. Thus, when the administration of the combination or composition of the present disclosure is done with freshly prepared mesenchymal stromal cells, and there is no requirement of cryopreserving the mesenchymal stromal cells, then the combination or composition need not contain DMSO. All such freshly prepared formulations of mesenchymal stromal cells comprising multiple electrolyte solution are also envisaged within the ambit of the combinations, compositions and kits of the present disclosure.

While the aforementioned process represents one of the ways by which the pooled MSC composition of the present disclosure can be obtained, a person skilled in the art understands that there are several other alternative methods through which a similar composition comprising the pooled MSCs, about 1 ml of multiple electrolyte solution such as plasmalyte A and about 1 ml of protein free, serum free, animal component free formulation of about 2.5% to 5% dimethyl sulfoxide (DMSO), can be prepared. As long as the final composition contains a total of about 20 to 30 million mesenchymal stromal cells pooled in equal proportions from at least 3 donors, and comprises about 1 ml of multiple electrolyte solution and about 1 ml of protein free, serum free, animal component free formulation of about 2.5% to 5% dimethyl sulfoxide (DMSO), all such compositions and respective methods of making such compositions fall within the ambit of the present disclosure.

In some embodiments, the pooling of MSCs for arriving at the composition of the present disclosure is similar to or identical to the method(s) described in PCT/IB2010/055424, which is incorporated as a reference in its entirety. However, as mentioned above, the method(s) described therein forms only one of the ways through which the composition of the present disclosure can be prepared.

On the other hand, the hyaluronic acid present as part of the combination therapy, product or kit of the present disclosure is a mid molecular weight hyaluronic acid.

In some embodiments, the molecular weight of the hyaluronic acid present as part of the combination therapy, product or kit of the present disclosure ranges from about 500,000 Dalton to about 730,000 Dalton.

Accordingly, in some embodiments, the molecular weight of the hyaluronic acid present as part of the combination therapy, product or kit of the present disclosure is about 500,000 Dalton, 550,000 Dalton, 600,000 Dalton, 650,000 Dalton, 700,000 Dalton or 730,000 Dalton.

In some embodiments, the amount of hyaluronic acid administered as part of the combination therapy of the present disclosure is about 2 ml.

In some embodiments, the hyaluronic acid administered comprises 20 mg of hyaluronic acid administered in 2 ml of buffered physiological sodium chloride having pH of 6.8 to 7.5.

Thus, as will be apparent to a person skilled in the art from a reading of the present disclosure, the criticality of the present disclosure lies in the specificity or selection of the features that results in the combination product or kit of the present disclosure. Therefore, the positive effects and improvements that are seen by a human subject suffering from osteoarthritis after undergoing treatment with the combination therapy of the present disclosure is a direct result of use of the combination product or kit having amalgamation of features that include:

specific number of pooled mesenchymal stromal cells present in the composition, number of donors that form the basis for arriving at the pooled mesenchymal stromal cells, presence of multiple electrolyte solution and protein free, serum free, animal component free formulation of dimethyl sulfoxide (DMSO), absence of human serum albumin (HSA), mid molecular weight of hyaluronic acid, and amounts of multiple electrolyte solution, dimethyl sulfoxide (DMSO) and hyaluronic acid present in the combination product or kit.

Accordingly, in some embodiments, the combination product or kit of the present disclosure comprises a composition comprising about 20 to 30 million mesenchymal stromal cells, about 1 ml of multiple electrolyte solution and about 1 ml of protein free, serum free, animal component free formulation of about 2.5% to 5% dimethyl sulfoxide (DMSO); and about 2 ml of hyaluronic acid, wherein the composition is devoid of human serum albumin (HSA).

In some embodiments, the combination product or kit of the present disclosure comprises a composition consisting of about 20 to 30 million mesenchymal stromal cells, about 1 ml of multiple electrolyte solution and about 1 ml of protein free, serum free, animal component free formulation of about 2.5% to 5% dimethyl sulfoxide (DMSO); and about 2 ml of hyaluronic acid, wherein the composition is devoid of human serum albumin (HSA).

In some embodiments, the combination product or kit of the present disclosure comprises a composition consisting of about 20 to 30 million mesenchymal stromal cells, about 1 ml of multiple electrolyte solution and about 1 ml of protein free, serum free, animal component free formulation of about 2.5% dimethyl sulfoxide (DMSO); and about 2 ml of hyaluronic acid, wherein the composition is devoid of human serum albumin (HSA).

In some embodiments, the combination product or kit of the present disclosure comprises a composition consisting of about 20 to 30 million mesenchymal stromal cells, about 1 ml of multiple electrolyte solution and about 1 ml of protein free, serum free, animal component free formulation of about 5% dimethyl sulfoxide (DMSO); and about 2 ml of hyaluronic acid, wherein the composition is devoid of human serum albumin (HSA).

Accordingly, in some embodiments, the combination product or kit of the present disclosure comprises a composition comprising about 25 million mesenchymal stromal cells, about 1 ml of multiple electrolyte solution and about 1 ml of protein free, serum free, animal component free formulation of about 2.5% to 5% dimethyl sulfoxide (DMSO); and about 2 ml of hyaluronic acid, wherein the composition is devoid of human serum albumin (HSA).

In some embodiments, the combination product or kit of the present disclosure comprises a composition consisting of about 25 million mesenchymal stromal cells, about 1 ml of multiple electrolyte solution and about 1 ml of protein free, serum free, animal component free formulation of about 2.5% to 5% dimethyl sulfoxide (DMSO); and about 2 ml of hyaluronic acid, wherein the composition is devoid of human serum albumin (HSA).

In some embodiments, the combination product or kit of the present disclosure comprises a composition consisting of about 25 million mesenchymal stromal cells, about 1 ml of multiple electrolyte solution and about 1 ml of protein free, serum free, animal component free formulation of about 2.5% dimethyl sulfoxide (DMSO); and about 2 ml of hyaluronic acid, wherein the composition is devoid of human serum albumin (HSA).

In some embodiments, the combination product or kit of the present disclosure comprises a composition consisting of about 25 million mesenchymal stromal cells, about 1 ml of multiple electrolyte solution and about 1 ml of protein free, serum free, animal component free formulation of about 5% dimethyl sulfoxide (DMSO); and about 2 ml of hyaluronic acid, wherein the composition is devoid of human serum albumin (HSA).

The specific features of the combination therapy, product and kit of the present disclosure provide for several advantages that are summarized as below:

The viability of the cells is maintained in spite of low volumes of the multiple electrolyte solution and protein free, serum free, animal component free formulation of DMSO, With the reduction in the overall volume of the composition and the hyaluronic acid, total amount of intraarticular injection volume is reduced thereby making it convenient for administration to the patient, The low volumes of the multiple electrolyte solution and protein free, serum free, animal component free formulation of DMSO present also ensure that the number of serious adverse events and toxicity to the cells are reduced, The stability of the product is not compromised as the product is stable for upto 18 months, There is a reduction in cryopreservation-induced cell stress and damage, and The absence of HSA makes the composition serum free.

As mentioned above, the combination product or kit of present disclosure is employed for the use in treatment of osteoarthritis. Accordingly, the present disclosure relates to the said use of the combination therapy of the present disclosure.

Thus, the present disclosure also relates to a combination of:

a composition comprising about 20 to 30 million mesenchymal stromal cells, multiple electrolyte solution and protein free, serum free, animal component free formulation of dimethyl sulfoxide (DMSO); and mid molecular weight hyaluronic acid, for use in a method of treating osteoarthritis in a human subject, wherein the composition is devoid of human serum albumin (HSA); wherein the mesenchymal stromal cells are bone marrow derived pooled mesenchymal cells obtained from pooling mesenchymal stromal cells from at least 3 donors; and wherein the composition or the hyaluronic acid or the combination, is administered via an ultrasound guided administration, through an intra-articular route.

In some embodiments related to the use of the combination, the osteoarthritis is a Grade II or Grade III osteoarthritis.

In some embodiments related to the use of the combination, the multiple electrolyte solution is Plasmalyte A.

In some embodiments related to the use of the combination, each of the composition and hyaluronic acid are administered through a single dose intra-articular administration.

In some embodiments related to the use of the combination, at least one or both of the composition and hyaluronic acid are administered through an ultrasound guided intra-articular administration.

In some embodiments related to the use of the combination, the composition and hyaluronic acid are administered simultaneously or sequentially.

In some embodiments related to the use of the combination, the hyaluronic acid is administered post 30 seconds to 30 minutes of the administration of the composition or within_1800_seconds of the administration of the composition.

In some embodiments related to the use of the combination, the combination provides improvement to the subject in osteoarthritic symptoms selected from a group comprising pain and stiffness; and improves or maintains quality parameters of respective cartilage in the subject, in relation to the subject prior to the administration of the said combination.

In some embodiments related to the use of the combination, the combination improves mean percentage change from baseline in at least one of WOMAC composite index score or WOMAC pain index score or WOMAC stiffness index score or WOMAC physical function index score or VAS score by at least about 10% in a span of about 6 months.

In some embodiments related to the use of the combination, the combination shows a mean difference in percentage change from baseline for at least one of WOMAC composite index score or WOMAC pain index score or WOMAC stiffness index score or WOMAC physical function index score or VAS score by at least about 15% at the 6 months timepoint.

In some embodiments related to the use of the combination, the combination shows a mean difference in percentage change from baseline for at least one of WOMAC composite index score or WOMAC pain index score or WOMAC stiffness index score or WOMAC physical function index score or VAS score by at least about 40% at the 12 months timepoint.

In some embodiments related to the use of the combination, the composition comprises 25 million mesenchymal stromal cells.

In some embodiments related to the use of the combination, the combination increases levels of anti-inflammatory marker interleukin-10 (IL-10) and decreases levels of disease progression marker crosslinked C-telopeptides of type II collagen (CTX-II) in the subject, in relation to the subject prior to the administration of the said combination.

Accordingly, the present disclosure also relates to a combination of:

a composition comprising about 20 to 30 million mesenchymal stromal cells, multiple electrolyte solution and protein free, serum free, animal component free formulation of dimethyl sulfoxide (DMSO); and mid molecular weight hyaluronic acid, for use in a method of increasing levels of anti-inflammatory marker interleukin-10 (IL-10) in a human subject suffering from osteoarthritis, wherein the combination is administered to the subject and the levels are increased in relation to the subject prior to administration of the said combination.

In some embodiments related to the use of the combination, the administration of the composition or the hyaluronic acid or both, is a single dose ultrasound guided administration, through an intra-articular route.

The present disclosure also relates to a combination of:

a composition comprising about 20 to 30 million mesenchymal stromal cells, multiple electrolyte solution and protein free, serum free, animal component free formulation of dimethyl sulfoxide (DMSO); and mid molecular weight hyaluronic acid, for use in a method of decreasing levels of disease progression marker crosslinked C-telopeptides of type II collagen (CTX-II) in a human subject suffering from osteoarthritis, wherein the combination is administered to the subject and the levels are decreased in relation to the subject prior to administration of the said combination.

In some embodiments related to the use of the combination, the administration of the composition or the hyaluronic acid or both, is a single dose ultrasound guided administration, through an intra-articular route.

The present disclosure therefore also relates to a combination of:

a composition comprising about 20 to 30 million mesenchymal stromal cells, multiple electrolyte solution and protein free, serum free, animal component free formulation of dimethyl sulfoxide (DMSO); and mid molecular weight hyaluronic acid, for use in a method of increasing levels of anti-inflammatory marker interleukin-10 (IL-10) and decreasing levels of disease progression marker crosslinked C-telopeptides of type II collagen (CTX-II) in a human subject suffering from osteoarthritis, wherein the combination is administered to the subject and the levels are increased and decreased, respectively, in relation to the subject prior to administration of the said combination.

In some embodiments related to the use of the combination, the administration of the composition or the hyaluronic acid or both, is a single dose ultrasound guided administration, through an intra-articular route.

Thus, the present disclosure also relates to a method of increasing levels of anti-inflammatory marker interleukin-10 (IL-10) in a human subject suffering from osteoarthritis, said method comprising administering to the subject the combination as described above; wherein the levels are increased in relation to the subject prior to administration of the said combination.

The present disclosure also relates to a method of decreasing levels of disease progression marker crosslinked C-telopeptides of type II collagen (CTX-II) in a human subject suffering from osteoarthritis, said method comprising administering to the subject the combination as described above; wherein the levels are decreased in relation to the subject prior to administration of the said combination.

Accordingly, the present disclosure also relates to a method of increasing levels of anti-inflammatory marker interleukin-10 (IL-10) and decreasing levels of disease progression marker crosslinked C-telopeptides of type II collagen (CTX-II) in a human subject suffering from osteoarthritis, said method comprising administering to the subject the combination as described above; wherein the levels are increased and decreased, respectively, in relation to the subject prior to administration of the said combination.

In some embodiments related to the methods of modulating (increasing and/or decreasing) levels of the described biomarkers, the administration of the composition or the hyaluronic acid or both, is a single dose ultrasound guided administration, through an intra-articular route.

While only a few of the embodiments are specifically recited in the context of the use of the combination, or the method of modulating levels of the described biomarkers, all other previously described embodiments that are recited within the present disclosure, in the context of describing the method of treatment of osteoarthritis, the combination therapy, the combination product or the kit, are equally applicable to the use of the combination envisaged herewith. It is only for the sake of brevity, that all such embodiments are not recited again here.

It is to be understood that the foregoing description is illustrative not a limitation. While considerable emphasis has been placed herein on particular features of this disclosure, it will be appreciated that various modifications can be made, and that many changes can be made in the preferred embodiments without departing from the principles of the disclosure. Those skilled in the art will recognize that the embodiments herein can be practiced with modification within the spirit and scope of the embodiments as described herein. Similarly, additional embodiments and features of the present disclosure will be apparent to one of ordinary skill in art based upon description provided herein.

Descriptions of well-known/conventional methods/steps and techniques are omitted so as to not unnecessarily obscure the embodiments herein. Further, the disclosure herein provides for examples illustrating the above-described embodiments, and in order to illustrate the embodiments of the present disclosure, certain aspects have been employed. The examples used herein for such illustration are intended merely to facilitate an understanding of ways in which the embodiments may be practiced and to further enable those of skill in the art to practice the embodiments. Accordingly, following examples should not be construed as limiting the scope of the embodiments herein.

EXAMPLES

Example 1—Efficacy and Safety of Single Intra-Articular Administration of the Combination Therapy of the Present Disclosure

Objectives

Primary Objective: To evaluate the efficacy following a single administration of the composition of the present disclosure administered by intra-articular injection in patients with osteoarthritis of knee. The composition comprises 25 million mesenchymal stromal cells, about 1 ml of multiple electrolyte solution and about 1 ml of 5% dimethyl sulfoxide (DMSO), and the composition is devoid of HSA.

Secondary Objective: To assess the safety and tolerability following a single administration of the said composition administered by intra-articular injection in patients with osteoarthritis of knee.

Patient Eligibility: Patients were eligible for enrolment in the study if they fulfilled the following criteria:

1. Male or female patients of age 40-65 years (both inclusive).
2. Patients with history of primary osteoarthritis of the knee characterized by pain which requires intakeof analgesics.
3. Patients who self-reported difficulty in at least one of the following activities attributed to knee pain: lifting and carrying groceries, walking 400 meters, getting in and out of a chair, getting up from squatting or cross leg position or going up and down stairs.
4. Patients who were on analgesic medication for OA, for 6 weeks based on Investigator's feedback.
5. Patients with radiological criteria—X-ray knee joint showing radiographic evidence of grade 2 to 3 osteoarthritis based on the Kellgren and Lawrence radiographic criteria (based on central radiologist report).
6. Patients who were willing to refrain from any other stromal cell treatment for 2 years during the study.
7. Female patients of childbearing age who were willing to use accepted methods of contraception during the course of the study.
8. Patients who were willing to provide written informed consent including audio-video consent.

Protocol: One hundred and forty-six patients were randomized to stromal cell (composition) and placebo group in a ratio of 1:1. Seventy-three patients received single dose of the composition comprising 25 million pooled MSCs in 1 ml CryoStor CS5+1 ml PlasmaLyte A followed by 2 ml hyaluronan (Stempeucel® group) and 73 patients received single dose of intra-articular injection of 2 ml placebo (1 ml CryoStor CS5+1 ml PlasmaLyte A) followed by 2 ml hyaluronan (Placebo group).

The study consisted of 9 visits:

Visit 1—Screening and clinical evaluation of the patient (−21 days to 0 days)

Visit 2—Randomization, Baseline activity and IMP administration (Day 0)

Visit 3—7 days (1 week)±3 days

Telephonic follow-up at 15±3 days

Visit 4—30 days (1 month)±7 days

Telephonic follow-up at 60±7 days

Visit 5—90 days (3 months)±7 days

Visit 6—180 days (6 months)±7 days

Telephonic follow-up at 270 days (9 months)±7 days

Visit 7—365 days (12 months)±14 days

Visit 8—540 days (18 months)±30 days

Visit 9—730 days (24 months)±30 days

Criteria for Evaluation

Primary endpoint: To assess the change from baseline to one year in WOMAC (Western Ontario and McMaster Universities Osteoarthritis) Osteoarthritis Composite Index score as compared to the placebo arm.

Secondary Endpoints:

To assess the change from baseline to two year in WOMAC (Western Ontario and McMaster Universities Osteoarthritis) Osteoarthritis Composite Index Score as compared to the placebo arm.

To assess the change from baseline to one year and two years follow-up as compared to the placebo arm in:

WOMAC OA Pain Index Score

WOMAC OA Stiffness Index Score

WOMAC OA Physical Function Index Score

Patient's Assessment of Osteoarthritis Pain by VAS Score [Osteoarthritis-Pain Visual Analog scale (VAS)]

Magnetic Resonance Imaging measurements (T2 mapping) to assess the quality of articular cartilage (depicts areas of altered composition and ultrastructure)

Magnetic Resonance Imaging measurements to measure the cartilage thickness & cartilage morphology at the mid points of the 20 pre-determined sub-regions across the two compartments of knee (medial femoral tibial joint & lateral femoral tibial joint)

Magnetic Resonance Imaging measurements to assess the cartilage volume.

Exploratory Endpoints:

Assessment of biomarkers: (IL-10 (serum) & CTX-II (urine))

Administration

The composition was administered intra-articularly, using blinded 5 ml syringe, under ultrasound guidance under all aseptic precautions and screen shot of the needle position in the intra articular space of the knee joint was documented.

The intra-articular injection was performed by PI/Co-PI using a 2.0 inch (5.1 cm) 20 gauge needle mostly as a medial or lateral para-patellar injection (an injection into the patello-femoral joint) but optimal joint positioning and site of needle insertion for the affected knee may vary according to the anatomic and pathologic conditions present. Patient remained hospitalized for the procedure for 24 hours in order to monitor for acute local or systromalic side effect or toxicity, if any.

After injecting IMP, the syringe was detached from the needle (which was not removed from the site of injection) and an injection of mid molecular weight hyaluronic acid was administered through the same needle, also under the ultrasound guidance. Hence, piercing of the needle intra-articularly was done only once.

Results

Of the 146 patients overall, 65 patients from the Stempeucel® and 68 patients from placebo group completed 12 month follow up period. Total 13 patients withdrew during the one year follow-up period due to death (one patient in Stempeucel®), lost to follow-up (3 patients in Stempeucel® and 1 patient in placebo group) and voluntary withdrawn (4 patients each in Stempeucel® and placebo group). Both the groups were comparable with respect to baseline parameters and demographic details. There were no major protocol deviations observed during the study. The primary analysis cohort was mITT for efficacy endpoints and safety cohort for safety endpoints.

Efficacy Results: The primary efficacy results was calculated on mITT and PP cohort. The WOMAC index is used to assess subjects with OA of the hip or knee joint using 24 parameters.

For the sake of comparison, Mean Difference and p values were relied upon.

Mean Difference: The mean difference measures the absolute difference between the mean value in two different groups. It gives the idea of how much difference there is between the averages of the experimental group (Stempeucel®) and control groups (placebo).

p-value: The p value is a statistical measure that indicates whether or not an effect is statistically significant. By convention, if the p value is below 0.05 (that is, there is less than a 5% probability that the results occurred by chance), it is considered that there probably is a real difference between treatments. If the p value is 0.001 or less (less than a 0.1% probability that the results occurred by chance), the result is seen as highly significant. If the p value shows that there is likely to be a difference between treatments, the confidence interval describes how big the difference in effect might be. Thus:

A p-value is a statistical measurement used to validate a hypothesis against observed data.

A p-value measures the probability of obtaining the observed results, assuming that the null hypothesis is true.

The lower the p-value, the greater the statistical significance of the observed difference.

A p-value of 0.05 or lower is generally considered statistically significant.

P-value can serve as an alternative to or in addition to preselected confidence levels for hypothesis testing.

WOMAC composite index score: The WOMAC composite index scores across the treatment groups were comparable at baseline. WOMAC composite index scores decreased substantially over the study period in Stempeucel® group.

The mean WOMAC composite index score showed a statistical significant improvement (p value<0.0001) in Stempeucel® compared to placebo at Day 180 and Day 365. Additionally, the statistical significance of <0.0001 was observed within the treatment groups at the earliest by Day 30 in mean WOMAC composite index score and the improvement in the symptoms was found to be consistent till Day 365 in Stempeucel® group. Whereas, worsening in mean WOMAC composite index score was seen in placebo group from Day 180 onwards. The mean percentage change from baseline in WOMAC composite index score showed a statistical significance improvement (p value<0.0001) in Stempeucel® compared to placebo at Day 180 and Day 365.

TABLE 1

WOMAC COMPOSITE INDEX - PERCENTAGE CHANGE FROM BASELINE

| Visit | Statistics | stempeucel ® (N = 73) | | placebo (N = 73) | | Mean difference (95% CI) | p-value |
| | | Actual | Percentage Change from baseline | Actual | Percentage Change from baseline | | |
|---|---|---|---|---|---|---|---|
| Baseline | n | 73 | | 73 | | | |
| | Mean | 1412.6 | | 1361.4 | | | |
| | SD | 336.59 | | 305.18 | | | |
| Visit 6 | n | 66 | 66 | 70 | 70 | −23.64 | <0.0001 |
| (6 Months) | Mean | 870.6 | −35.0 | 1187.7 | −11.3 | (−32.88--14.40) | |
| | SD | 297.87 | 21.64 | 469.69 | 31.61 | | |
| Visit 7 | n | 65 | 65 | 68 | 68 | −45.60 | <.0001 |
| (12 Months) | Mean | 741.3 | −44.3 | 1363.5 | 1.3 | (−55.97--35.23) | |
| | SD | 346.13 | 24.33 | 488.62 | 34.94 | | |

WOMAC pain index score: The WOMAC pain index scores across the treatment groups were comparable at baseline. WOMAC pain index scores decreased substantially over the study period in Stempeucel® group.

The mean WOMAC pain index score showed a statistical significant improvement (p value<0.0001) in Stempeucel® compared to placebo at Day 180 and Day 365. Additionally, the statistical significance of <0.0001 was observed within the treatment groups at the earliest by Day 30 in mean WOMAC pain index score and the improvement in the symptoms was found to be consistent till Day 365 in Stempeucel® group. Whereas, worsening in mean WOMAC pain index score was seen in placebo group from Day 180 onwards. The mean percentage change from baseline in WOMAC pain index score showed a statistical significance improvement (p value<0.0001) in Stempeucel® compared to placebo at Day 180 and Day 365.

TABLE 2

WOMAC PAIN INDEX - PERCENTAGE CHANGE FROM BASELINE

| | | stempeucel ® (N = 73) | | placebo (N = 73) | | | |
|---|---|---|---|---|---|---|---|
| Visit | Statistics | Actual | Percentage Change from baseline | Actual | Percentage Change from baseline | Mean difference (95% CI) | p-value |
| Baseline | n | 73 | | 73 | | | |
| | Mean | 295.3 | | 282.0 | | | |
| | SD | 76.03 | | 67.70 | | | |
| Visit 6 | n | 66 | 66 | 70 | 70 | −26.91 | <0.0001 |
| (6 Months) | Mean | 177.1 | −35.6 | 250.7 | −8.7 | (−36.29--17.53) | |
| | SD | 61.57 | 24.00 | 93.43 | 30.67 | | |
| Visit 7 | n | 65 | 65 | 68 | 68 | −46.34 | <.0001 |
| (12 Months) | Mean | 150.2 | −45.4 | 279.1 | 1.0 | (−56.94--35.73) | |
| | SD | 71.06 | 24.85 | 101.97 | 35.73 | | |

WOMAC stiffness index score: The WOMAC stiffness index scores across the treatment groups were comparable at baseline. WOMAC stiffness index scores decreased substantially over the study period in Stempeucel® group.

The mean WOMAC stiffness index score showed a statistical significant improvement (p value=<0.0001) in Stempeucel® compared to placebo at Day 180 and Day 365. Additionally, the statistical significance of <0.0001 was observed within the treatment groups at the earliest by Day 30 in mean WOMAC stiffness index score and the improvement in the symptoms was found to be consistent till Day 365 in Stempeucel® group. Whereas, worsening in mean WOMAC stiffness index score was seen in placebo group from Day 180 onwards. The mean percentage change from baseline in WOMAC stiffness index score showed a statistical significance improvement (p value<0.0001) in Stempeucel® compared to placebo at Day 180 and Day 365.

TABLE 3

WOMAC STIFFNESS INDEX - PERCENTAGE CHANGE FROM BASELINE

| | | stempeucel ® (N = 73) | | placebo (N = 73) | | | |
|---|---|---|---|---|---|---|---|
| Visit | Statistics | Actual | Percentage Change from baseline | Actual | Percentage Change from baseline | Mean difference (95% CI) | p-value |
| Baseline | n | 73 | | 73 | | | |
| | Mean | 114.6 | | 109.4 | | | |
| | SD | 36.76 | | 35.17 | | | |

TABLE 3-continued

| WOMAC STIFFNESS INDEX - PERCENTAGE CHANGE FROM BASELINE | | | | | | | |
| --- | --- | --- | --- | --- | --- | --- | --- |
| | | stempeucel ® (N = 73) | | placebo (N = 73) | | | |
| Visit | Statistics | Actual | Percentage Change from baseline | Actual | Percentage Change from baseline | Mean difference (95% CI) | p-value |
| Visit 6 | n | 66 | 66 | 70 | 70 | −31.90 | <.0001 |
| (6 Months) | Mean | 68.9 | −35.6 | 98.3 | −3.7 | (−44.72--19.08) | |
| | SD | 31.45 | 27.98 | 41.40 | 45.12 | | |
| Visit 7 | n | 65 | 65 | 68 | 68 | −55.12 | <.0001 |
| (12 Months) | Mean | 61.0 | −39.8 | 113.1 | 15.4 | (−79.35--30.89) | |
| | SD | 31.61 | 47.00 | 42.08 | 87.40 | | |

WOMAC physical function index score: The WOMAC physical function index scores across the treatment groups were comparable at baseline. WOMAC physical function index scores decreased substantially over the study period in Stempeucel® group.

The mean WOMAC physical function index score showed a statistical significant improvement (p value=<0.0001) in Stempeucel® compared to placebo at Day 180 and Day 365. Additionally, the statistical significance of <0.0001 was observed within the treatment groups at the earliest by Day 30 in mean WOMAC physical function index score and the improvement in the symptoms was found to be consistent till Day 365 in Stempeucel® group. Whereas, worsening in mean WOMAC physical function index score was seen in placebo group from Day 180 onwards. The mean percentage change from baseline in WOMAC physical function index score showed a statistical significance improvement (p value<0.0001) in Stempeucel® compared to placebo at Day 180 and Day 365.

TABLE 4

| WOMAC PHYSICAL FUNCTION INDEX - PERCENTAGE CHANGE FROM BASELINE | | | | | | | |
| --- | --- | --- | --- | --- | --- | --- | --- |
| | | stempeucel ® (N = 73) | | placebo (N = 73) | | | |
| Visit | Statistics | Actual | Percentage Change from baseline | Actual | Percentage Change from baseline | Mean difference (95% CI) | p-value |
| Baseline | n | 73 | | 73 | | | |
| | Mean | 1002.7 | | 969.9 | | | |
| | SD | 236.47 | | 223.40 | | | |
| Visit 6 | n | 66 | 66 | 70 | 70 | −22.60 | <0.0001 |
| (6 Months) | Mean | 624.6 | −34.6 | 838.7 | −12.0 | (−32.07--13.12) | |
| | SD | 216.54 | 21.24 | 340.70 | 33.00 | | |
| Visit 7 | n | 65 | 65 | 68 | 68 | −45.63 | <.0001 |
| (12 Months) | Mean | 530.1 | −44.1 | 971.3 | 1.5 | (−56.27--34.98) | |
| | SD | 251.66 | 24.09 | 353.47 | 36.43 | | |

US 12,661,377 B2

27

Pain assessment by VAS score: The VAS scores across the treatment groups were comparable at baseline. VAS scores decreased substantially over the study period in Stempeucel® group.

The mean VAS score showed a statistical significant improvement (p value<0.0001) in Stempeucel® compared to placebo at Day 180 and Day 365. Additionally, the statistical significance of <0.0001 was observed within the treatment groups at the earliest by Day 30 in mean VAS score and the improvement was found to be consistent till Day 365 in Stempeucel® group. Whereas, worsening in mean VAS score was seen in placebo group from Day 180 onwards. The mean percentage change from baseline in VAS score showed a statistical significance improvement (p value<0.0001) in Stempeucel® compared to placebo at Day 180 and Day 365.

28

For Medial FT Compartment (Femoral Condyle) Region

Table 6 below represents the Analysis of T2 mapping Medial FT compartment (Femoral condyle) in mITT cohort.

For deep cartilage, the mean (SD) score at baseline was 35.7 (7.68) ms and 39.2 (8.04) ms in Stempeucel® and placebo group, respectively. The mean (SD) score at Day 180 was 37.8 (8.72) ms and 39.2 (8.07) ms in Stempeucel® and placebo group, respectively. The change from baseline in mean (SD) deep cartilage score at Day 180 was increased by 1.6 (6.77) ms and decreased by 0.4 (7.94) ms in Stempeucel® and placebo group, respectively, which was found to be statistically non-significant with a p-value of 0.4436 when the comparison between the groups was conducted. The mean (SD) score at Day 365 was 36.1 (7.79) ms and

TABLE 5

VAS- PERCENTAGE CHANGE FROM BASELINE

| Visit | Statistics | stempeucel ® (N = 73) | | placebo (N = 73) | | Mean difference (95% CI) | p-value |
|---|---|---|---|---|---|---|---|
| | | Actual | Percentage Change from baseline | Actual | Percentage Change from baseline | | |
| Baseline | n | 73 | | 73 | | | |
| | Mean | 66.1 | | 65.0 | | | |
| | SD | 13.96 | | 13.09 | | | |
| Visit 6 | n | 66 | 66 | 70 | 70 | −17.62 | <.0001 |
| (6 Months) | Mean | 40.3 | −37.0 | 52.5 | −19.4 | (−26.20--9.04)) | |
| | SD | 15.47 | 25.94 | 19.54 | 24.67 | | |
| Visit 7 | n | 65 | 65 | 68 | 68 | −41.58 | <.0001 |
| (12 Months) | Mean | 33.5 | −46.8 | 61.1 | −5.2 | (−51.86--31.29) | |
| | SD | 17.34 | 28.53 | 21.85 | 31.30 | | |

Magnetic Resonance Imaging measurements (T2 mapping) to assess the quality of articular cartilage (depicts areas of altered composition and ultrastructure): The medial T2 mapping evaluates the status of the cartilage matrix and identifies biochemical changes associated with the early stages of OA. The T2 relaxation time of articular cartilage is a function of both the water content and collagen ultrastructure of the tissue. Measurement of the spatial distribution of the T2 relaxation time reveals areas of increased or decreased water content that correlates with cartilage damage. Increase of water content and damage to collagen network leads to higher T2 values.

The change from baseline in magnetic resonance imaging measurements (T2 mapping) was assessed to understand the quality of articular cartilage (depicts areas of altered composition and ultrastructure). The superficial cartilage, intermediate cartilage, deep cartilage and average cartilage score of both medial femoro-tibial and lateral femoro-tibial compartments were measured during the study.

47.0 (75.12) ms in Stempeucel® and placebo group, respectively. At Day 365, the change from baseline in mean (SD) deep cartilage score was decreased by 0.6 (7.29) ms and increased by 10.8 (79.53) ms in Stempeucel® and placebo group, respectively, which was found to be statistically non-significant with a p-value of 0.7064 when the comparison between the groups was conducted. Additionally, the within group statistical significance was observed of <0.0001 in Stempeucel® and statistical non-significance was observed of 0.7643 in placebo was observed at Day 180 and within group statistical non-significance was observed of 0.6188 in Stempeucel® and statistical significance was observed of <0.0001 in placebo at Day 365 in mean deep cartilage score. Hence, it can be concluded that in deep cartilage there is worsening of the cartilage in the placebo group, the mean scores increasing from 39.2 ms at baseline to 47.0 ms at Day 365, but the difference between the groups was not significant.

TABLE 6

ANALYSIS OF T2 MAPPING - MEDIAL FT COMPARTMENT (FEMORAL CONDYLE)

| | | | stempeucel (N = 73) | | placebo (N = 73) | | |
|---|---|---|---|---|---|---|---|
| Parameter | Visit | Statistics | Actual | Change from Baseline | Actual | Change from Baseline | p-value |
| Deep Cartilage | Baseline | n | 62 | | 66 | | |
| | | Mean | 35.7 | | 39.2 | | |
| | | SD | 7.68 | | 8.04 | | |
| | | Minimum | 21 | | 18 | | |
| | | Q1 | 30.7 | | 33.5 | | |
| | | Median | 35.4 | | 39.0 | | |
| | | Q3 | 39.0 | | 43.9 | | |
| | | Maximum | 56 | | 58 | | |
| | Visit 6 | n | 43 | 40 | 43 | 42 | 0.4436@ |
| | (Day 180) | Mean | 37.8 | 1.6 | 39.2 | −0.4 | |
| | | SD | 8.72 | 6.77 | 8.07 | 7.94 | |
| | | Minimum | 21 | −6 | 25 | −20 | |
| | | Q1 | 31.6 | −2.5 | 33.8 | −4.2 | |
| | | Median | 35.5 | −0.4 | 38.0 | −1.0 | |
| | | Q3 | 44.1 | 3.8 | 44.7 | 4.2 | |
| | | Maximum | 59 | 21 | 57 | 17 | |
| | | p-value | <0.0001$ | | 0.7643$ | | |
| | Visit 7 | n | 48 | 41 | 48 | 42 | 0.7064@ |
| | (Day 365) | Mean | 36.1 | −0.6 | 47.0 | 10.8 | |
| | | SD | 7.79 | 7.29 | 75.12 | 79.53 | |
| | | Minimum | 21 | −24 | 23 | −22 | |
| | | Q1 | 30.6 | −4.5 | 33.2 | −5.3 | |
| | | Median | 35.9 | −1.7 | 36.8 | −2.3 | |
| | | Q3 | 40.4 | 3.3 | 41.4 | 4.8 | |
| | | Maximum | 55 | 15 | 555 | 511 | |
| | | p-value | 0.6188$ | | <0.0001$ | | |

Magnetic Resonance Imaging Measurements to Measure the Cartilage Thickness & Cartilage Morphology at the Mid Points of the Pre-Determined Sub-Regions Across the Two Compartments of Knee (Medial Femoral Tibial Joint & Lateral Femoral Tibial Joint):

Lateral Femoral Tibial compartment: There was significant (p value=0.0003) increase in mean values by 1.762 in Stempeucel® group at Day 365, and in the placebo group there was also significant (p value=0.0008) increase by 1.973 at Day 365. The mean values were not significant between groups at Day 365.

Medial Femoral Tibial compartment—There was significant (p value=0.0289) increase in mean values by 1.292 in Stempeucel® group at Day 365, and in the placebo group there was also significant (p value=0.0113) increase by 1.867 at Day 365. The mean values were not significant between groups at Day 365.

Total score—There was significant (p value=0.0015) increase in mean values by 3.054 in Stempeucel® group at Day 365, and in the placebo group there was also significant (p value=0.0010) increase by 3.840 at Day 365. The mean values were not significant between groups at Day 365. Hence, there is no change in cartilage thickness at Day 365 in both the groups (Table 7 below).

TABLE 7

ANALYSIS OF CARTILAGE THICKNESS

| | | | stempeucel ® (N = 73) | | placebo (N = 73) | | |
|---|---|---|---|---|---|---|---|
| Parameter | Visit | Statistics | Actual | Change from baseline | Actual | Change from baseline | p-value |
| Lateral Femoral Tibial (LFT) compartment | Baseline | Mean | 21.233 | | 21.515 | | |
| | | SD | 4.2324 | | 4.3165 | | |
| | Visit 6 (Day 180) | Mean | 22.672 | 2.179 | 23.369 | 2.015 | 0.8215* |
| | | SD | 3.1042 | 3.2931 | 3.1292 | 3.8695 | |
| | Visit 7 (Day 365) | Mean | 22.955 | 1.762 | 23.615 | 1.973 | 0.7658* |
| | | SD | 3.1616 | 3.2839 | 3.3518 | 3.6673 | |
| Medial Femoral Tibial (MFT) compartment | Baseline | Mean | 18.306 | | 18.882 | | |
| | | SD | 4.7304 | | 5.0179 | | |
| | Visit 6 (Day 180) | Mean | 19.144 | 1.591 | 19.788 | 1.446 | 0.8670* |
| | | SD | 4.2053 | 4.1002 | 4.0946 | 4.4320 | |
| | Visit 7 (Day 365) | Mean | 19.306 | 1.292 | 21.106 | 1.867 | 0.8146@ |
| | | SD | 3.4448 | 4.1421 | 3.8798 | 4.7377 | |

TABLE 7-continued

ANALYSIS OF CARTILAGE THICKNESS

| Parameter | Visit | Statistics | stempeucel ® (N = 73) | | placebo (N = 73) | | p-value |
|---|---|---|---|---|---|---|---|
| | | | Actual | Change from baseline | Actual | Change from baseline | |
| Total score | Baseline | Mean | 39.539 | | 40.398 | | |
| | | SD | 7.8008 | | 8.1987 | | |
| | Visit 6 | Mean | 41.816 | 3.770 | 43.157 | 3.462 | 0.8188* |
| | (Day 180) | SD | 6.3737 | 6.5507 | 5.9201 | 6.7874 | |
| | Visit 7 | Mean | 42.261 | 3.054 | 44.721 | 3.840 | 0.5776* |
| | (Day 365) | SD | 5.2078 | 6.5717 | 5.7778 | 7.2816 | |

Cartilage Volume:

Lateral Femoral Tibial compartment: There was significant (p value<0.0001) increase in mean values by 107.2 in Stempeucel® group at Day 365, and in the placebo group there was also significant (p value<0.0001) increase by 143.7 at Day 365. The mean values were not significant between groups at Day 365.

Medial Femoral Tibial compartment—There was significant (p value=0.0195) increase in mean values by 60.0 in Stempeucel® group at Day 365, and in the placebo group there was also significant (p value=0.0007) increase by 102.8 at Day 365. The mean values were not significant between groups at Day 365.

Total score—There was significant (p value<0.0001) increase in mean values by 167.3 in Stempeucel® group at Day 365, and in the placebo group there was also significant (p value<0.0001) increase by 246.5 at Day 365. The mean values were not significant between groups at Day 365. At Day 180 there was significant (p value<0.0001) decrease in mean values by 53.9 in Stempeucel® group and significant (p value<0.0001) decrease in mean value by 271.6 in placebo group. The difference between the groups was approaching significance at Day 180 (p=0.0555) (Table 8).

Additional analysis performed on total score of cartilage volume using Generalized Estimating Equation (GEE) method showed the difference in the cartilage total volume value between two groups over 1 year. In the Stempeucel® group there is increase in average cartilage total volume of 34.07 as compared to placebo group irrespective of time which is statistically not significant (Table 8A below, respectively).

GEE analysis shows the difference in cartilage volume in lateral femoro-tibial compartment between two groups over 1 year. In Stempeucel® group there is increase in cartilage volume of 25.97 as compared to placebo group irrespective of time which is statistically not significant. Cartilage volume values are increasing by 0.26 as the time increases in the Stempeucel® group as compared to placebo which is not statistically significant.

GEE analysis shows the difference in the cartilage total volume value between two groups over 1 year. In the Stempeucel® group there is increase in average cartilage total volume of 34.07 as compared to placebo group irrespective of time which is statistically not significant. The volume of the cartilage total value is decreasing by 1.61 as the time increases in Stempeucel® as compared to placebo group however which is not statistically significant.

TABLE 8

ANALYSIS OF CARTILAGE VOLUME

| Parameter | Visit | Statistics | stempeucel ® (N = 73) | | placebo (N = 73) | | p-value |
|---|---|---|---|---|---|---|---|
| | | | Actual | Change from baseline | Actual | Change from baseline | |
| Medial Femoral | Baseline | Mean | 221.4 | | 240.7 | | |
| Tibial (MFT) | | SD | 162.79 | | 134.95 | | |
| compartment | Visit 6 | Mean | 157.7 | −35.7 | 149.0 | −99.9 | 0.0883@ |
| | (Day 180) | SD | 158.67 | 161.57 | 174.02 | 185.00 | |
| | Visit 7 | Mean | 284.2 | 60.0 | 356.1 | 102.8 | 0.3773@ |
| | (Day 365) | SD | 161.43 | 168.00 | 174.76 | 176.15 | |
| Lateral Femoral | Baseline | Mean | 419.3 | | 431.6 | | |
| Tibial (LFT) | | SD | 136.93 | | 123.49 | | |
| compartment | Visit 6 | Mean | 389.1 | −18.1 | 265.0 | −171.7 | 0.0953@ |
| | (Day 180) | SD | 385.39 | 390.48 | 242.18 | 285.79 | |
| | Visit 7 | Mean | 514.6 | 107.2 | 539.4 | 143.7 | 0.2042* |
| | (Day 365) | SD | 153.22 | 134.12 | 147.46 | 129.08 | |
| Total score | Baseline | Mean | 640.7 | | 672.4 | | |
| | | SD | 244.47 | | 205.51 | | |
| | Visit 6 | Mean | 546.8 | −53.9 | 414.1 | −271.6 | 0.0555@ |
| | (Day 180) | SD | 474.30 | 484.84 | 386.36 | 438.35 | |
| | Visit 7 | Mean | 798.8 | 167.3 | 895.6 | 246.5 | 0.1627* |
| | (Day 365) | SD | 269.31 | 255.53 | 258.79 | 265.54 | |

TABLE 8A

| | | |
|---|---|---|
| GEE ANALYSIS | | |
| | Estimate (95% CI) | p value |
| Time Group | 19.64 (3.09, 36.19) | 0.020 |
| stempeucel Group*Time | 34.07 (−63.08, 131.22) | 0.492 |
| stempeucel ® | −1.61 (−11.69, 8.47) | 0.755 |

Biomarkers:

Interleukin 10 (IL-10): In Stempeucel® group there was mean increase by 0.376 pg/mol at Day 30 which was significant (p=0.0313), increase by 0.323 pg/mol at Day 90 (p=0.0625) and increase by 0.051 pg/mol at Day 365 (p=0.0625). In placebo group there was increase by 0.267 pg/mol at Day 30 which was significant (p=0.0313), decrease by 0.342 pg/mol at Day 90 (p=0.0625) and significant decrease by 0.228 pg/mol at Day 365 (p=0.0156). However, the difference between the groups was not significant at any time point. Hence, the IL-10 values increased by 0.051 pg/mol in Stempeucel® group and decreased by 0.228 pg/mol in placebo group at Day 365. The mean difference between the groups was 0.28 pg/mol, which was not significant (p=0.4546) (Table 9).

The details are as follows:

The mean (SD) serum levels of IL-10 at baseline was 0.083 (0.44) pg/ml and 0.558 (4.60) pg/ml in Stempeucel® and placebo group respectively. The mean (SD) serum levels of IL-10 at Day 7 was 0.185 (0.91) pg/ml and 0.578 (2.32) pg/ml in Stempeucel® and placebo group. The change from baseline in mean (SD) serum levels of IL-10 at Day 7 was increased by 0.101 (1.03) pg/ml and 0.012 (5.24) pg/ml in Stempeucel® and placebo group respectively. The mean difference (95% CI) of 0.09 (−1.16, 1.34) was observed with no statistical significance for Stempeucel® compared to placebo (p=0.2405) when the comparison between the groups was conducted.

The mean (SD) serum levels of IL-10 at Day 30 was 0.462 (2.00) pg/ml and 0.842 (5.01) pg/ml in Stempeucel® and placebo group. At Day 30, the change from baseline in mean (SD) serum levels of IL-10 was increased by 0.376 (2.07) pg/ml and 0.267 (6.94) pg/ml in Stempeucel® and placebo group respectively. The mean difference (95% CI) of 0.11 (−1.61, 1.82) was observed with no statistical significance for Stempeucel® compared to placebo (p=0.9800) when the comparison between the groups was conducted. The mean (SD) serum levels of IL-10 at Day 90 was 0.415 (1.59) pg/ml and 0.305 (1.18) pg/ml in Stempeucel® and placebo group. Further, the change from baseline in mean (SD) serum levels of IL-10 at Day 90 was increased by 0.323 (1.62) pg/ml and decreased by 0.342 (4.26) pg/ml in Stempeucel® and placebo group respectively. The mean difference (95% CI) of 0.66 (−0.45, −1.78) was observed with no statistical significance for Stempeucel® compared to placebo (p=0.6137) when the comparison between the groups was conducted. The mean (SD) serum levels of IL-10 at Day 180 was 0.029 (0.22) pg/ml and 0.114 (0.87) pg/ml in Stempeucel® and placebo group. The change from baseline in mean (SD) serum levels of IL-10 at Day 180 was decreased by 0.079 (0.56) pg/ml and 0.562 (5.21) pg/ml in Stempeucel® and placebo group respectively. The mean difference (95% CI) of 0.48 (−0.91, 1.87) was observed with no statistical significance for Stempeucel® compared to placebo (p=0.4519) when the comparison between the groups was conducted.

The mean (SD) serum levels of IL-10 at Day 365 was 0.143 (0.48) pg/ml and 0.586 (2.74) pg/ml in Stempeucel® and placebo group. Similarly, the change from baseline in mean (SD) serum levels of IL-10 at Day 365 was increased by 0.051 (0.71) pg/ml and decreased by 0.228 (6.33) pg/ml in Stempeucel® and placebo group respectively. The mean difference (95% CI) of 0.28 (−1.48, 2.03) was observed with no statistical significance for Stempeucel® compared to placebo (p=0.4546) when the comparison between the groups was conducted. Overall, the statistical significance of <0.0001 was not observed between the treatment groups in mean serum levels of IL-10.

Additionally, the statistical significance of <0.0001 was not observed within the treatment groups in mean serum levels of IL-10 (except at Day 30 in both groups [p-value of 0.0313] and Day 365 in placebo group [p-value=0.00156]) was observed.

Hence, it can be concluded that serum IL-10 levels in placebo group decreased by 0.228 pg/ml at Day 365 days follow up within the group which was statistically significant (p=0.0156). In the Stempeucel® group it increased by 0.051 pg/ml at Day 365 within the group which was not significant (p=0.0625). However, the difference between the groups was not significant at Day 365.

C-telopeptide of type II collagen (CTX-II) (urine): In Stempeucel® group the mean values decreased by 44.784 ng/mmol at Day 90 which was significant (p<0.0001) whereas in placebo group it increased by 83.612 ng/mmol at Day 90 (p<0.0001). At Day 365, the mean values increased by 32.568 ng/mmol in Stempeucel® group and increased by 49.354 ng/mmol in placebo group. The differences between the groups was not significant at any time point. Additional adhoc analysis performed using GEE method showed the difference in CTX II value between two groups over 1 year period. In Stempeucel® group there is decrease in CTX II levels of 7.79 ng/mmol as compared to placebo group irrespective of time which is statistically not significant (Table 9).

TABLE 9

| | | | ANALYSIS OF BIOMARKERS (IL-10[SERUM] & CTX-II [URINE] | | | | | |
|---|---|---|---|---|---|---|---|---|
| | | | stempeucel ® (N = 73) | | placebo (N = 73) | | | |
| Parameter | Visit | Statistics | Actual | Change from baseline | Actual | Change from baseline | Mean difference (95% CI) | p-value |
| IL-10 (serum) | Baseline | Mean | 0.083 | | 0.558 | | | |
| | | SD | 0.4469 | | 4.6058 | | | |

TABLE 9-continued

| | | | stempeucel ® (N = 73) | | placebo (N = 73) | | | |
|---|---|---|---|---|---|---|---|---|
| Parameter | Visit | Statistics | Actual | Change from baseline | Actual | Change from baseline | Mean difference (95% CI) | p-value |
| | Visit 3 | Mean | 0.185 | 0.101 | 0.578 | 0.012 | 0.09 | 0.2405@ |
| | (Day 7) | SD | 0.9122 | 1.0326 | 2.3241 | 5.2495 | (−1.16-1.34) | |
| | Visit 4 | Mean | 0.462 | 0.376 | 0.842 | 0.267 | 0.11 | 0.9800@ |
| | (Day 30) | SD | 2.0011 | 2.0721 | 5.0159 | 6.9474 | (−1.61-1.82) | |
| | Visit 5 | Mean | 0.415 | 0.323 | 0.305 | −0.342 | 0.66 | 0.6137@ |
| | (Day 90) | SD | 1.5968 | 1.6238 | 1.1859 | 4.2610 | (−0.45-1.78) | |
| | Visit 6 | Mean | 0.029 | −0.079 | 0.114 | −0.562 | 0.48 | 0.4519@ |
| | (Day 180) | SD | 0.2205 | 0.5601 | 0.8749 | 5.2131 | (−0.91-1.87) | |
| | Visit 7 | Mean | 0.143 | 0.051 | 0.586 | −0.228 | 0.28 | 0.4546@ |
| | (Day 365) | SD | 0.4861 | 0.7182 | 2.7421 | 6.3325 | (−1.48-2.03) | |
| CTX-II (urine) | Baseline | Mean | 462.104 | | 417.845 | | | |
| | | SD | 372.5276 | | 235.2729 | | | |
| | Visit 3 | Mean | 576.840 | 113.873 | 526.956 | 113.592 | 0.28 | 0.7725@ |
| | (Day 7) | SD | 597.8259 | 524.0595 | 539.3486 | 499.1582 | (−168.33-168.89) | |
| | Visit 4 | Mean | 480.365 | 9.834 | 446.742 | 25.752 | −15.92 | 0.6762@ |
| | (Day 30) | SD | 430.4995 | 467.3798 | 301.6967 | 278.0614 | (−143.76-111.93) | |
| | Visit 5 | Mean | 433.682 | −44.784 | 510.056 | 83.612 | −128.40 | 0.1384@ |
| | (Day 90) | SD | 351.8456 | 400.9378 | 488.9263 | 443.2939 | (−275.53-18.74) | |
| | Visit 6 | Mean | 529.805 | 62.448 | 426.187 | 5.252 | 57.20 | 0.7952@ |
| | (Day 180) | SD | 802.5774 | 774.3038 | 517.4391 | 487.6463 | (−180.59-294.98) | |
| | Visit 7 | Mean | 508.643 | 32.568 | 449.064 | 49.354 | −16.79 | 0.9260@ |
| | (Day 365) | SD | 371.9569 | 428.2594 | 410.6354 | 424.6405 | (−186.21-152.63) | |

Additional Analysis Done for CTX II Biomarker:

GEE analysis shows the difference in CTX-II value between two groups over 1 year. Results are as provided below:

TABLE 10

CTX II (urine) ANALYSIS
Group

| | placebo | | stempeucel ® | |
|---|---|---|---|---|
| Days | Mean | SD | Mean | SD |
| 1 | 434.84 | 224.99 | 462.10 | 372.53 |
| 7 | 500.54 | 366.68 | 486.50 | 375.03 |
| 30 | 446.74 | 301.70 | 452.40 | 324.13 |
| 90 | 474.14 | 351.19 | 440.30 | 350.42 |
| 180 | 376.36 | 284.63 | 413.11 | 357.56 |
| 365 | 409.52 | 309.17 | 508.64 | 371.96 |

TABLE 10A

GEE ANALYSIS RESULTS

| | Estimate (95% CI) | p value |
|---|---|---|
| Time Group | −0.46 (−0.99, 0.06) | 0.082 |
| stempeucel ® Group*Time | −7.79 (−96.18, 80.60) | 0.863 |
| stempeucel ® | 0.26 (−0.07, 0.59) | 0.120 |

In Stempeucel® group there is decrease in CTX-II levels of 7.79 ng/mmol as compared to placebo group irrespective of time which is statistically not significant (Tables 10 and 10A).

Safety Results:

A total of 82 adverse events (AEs) were reported in 44 patients. There was 49 AEs in 24 patients in the Stempeucel® group and 33 AEs in 20 patients in the placebo group. All the AEs observed in both treatment groups were treatment emergent except for 3 AEs (pyrexia, vomiting and anaemia) in placebo group which occurred before administration of study drug. Most of the AEs were mild in nature and unrelated to study drug. None of the patient from both treatment groups was withdrawn from the study due to AE.

Conclusion

In summary, the efficacy data showed there is significant improvement in patient reported outcomes like WOMAC & VAS scores in Stempeucel® group. The primary end point of the study—WOMAC composite index score were significant starting from 6 months follow up to 12 months follow up (p<0.0001) in Stempeucel® group as compared to placebo group.

Similar results were seen in the WOMAC subscores (pain, stiffness & physical function) and VAS score, which were significant starting from 6 months follow up to 12 months follow up (p<0.0001) in Stempeucel® group as compared to the placebo group.

T2 mapping done by MRI to see the quality of cartilage (hydration & collagen matrix) shows that there is no worsening of the deep cartilage in the medial compartment of the knee in Stempeucel® group as compared to placebo group where there is significant and gradual worsening of the cartilage seen within the group. There is increase in average cartilage total volume of 34.07 ms in Stempeucel® group as compared to placebo group irrespective of time which is statistically not significant.

Biomarkers analysis showed that IL-10 values (anti-inflammatory marker) increased by 0.051 pg/mol in Stempeucel® group and decreased by 0.228 pg/mol in placebo group at Day 365 (mean difference 0.28 pg/mol), which was not significant. Further in Stempeucel® group there is decrease in CTX II levels (a measure of C-terminal cross-linked telopeptide type II collagen secreted into urine and indicative of disease progression) of 7.79 ng/mmol as compared to placebo group irrespective of time which is statistically not significant.

Based on the above findings, it can be concluded that Stempeucel® is safe and effective in treating KL Grade II and Grade III Osteoarthritis of knee.

Example 2—TSP-2 Secretion in the Presence of Inflammatory Cytokines (IFN-γ and TNF-α)

Objective

To evaluate potential secretion of TSP-2 by Stempeucel® in inflammatory conditions.

Priming of MSCs with inflammatory cytokines was carried out to mimic the OA clinical condition, where the Stempeucel® will be administered in the intra articular space in the knee joints with high level of inflammation.

Stempeucel® (25 million cells/ml of CS5) from 8 batches were seeded at cell concentration of 1.0 million cells in 10 ml of complete media per T75 flask in duplicate. One set of cultures were primed with IFN-γ (10 ng/ml) and TNF-α (15 ng/ml) after 24 hrs of seeding and incubated further up to 96 hrs from seeding.

Another set cultured for 96 hrs without priming with IFN-γ and TNF-α and termed from here on as "unprimed".

Condition media samples collected from both the primed and unprimed cultures at 48 hr, 72 hr and 96 hr time points from seeding. Collected condition media samples were analyzed for TSP-2 ELISA.

Results

The concentration of TSP-2 in unprimed cells varies between 4-16 ng/ml, 12-30 ng/ml and 17-29 ng/ml at 48,72 and 96 hrs respectively (FIG. 1A. Table 11). Priming reduces the concentration of TSP-2 in all the batches at all the time points (FIG. 1B, ranges from 2-7 ng/ml). There is an average difference of 5 folds in TSP-2 secretion between primed and unprimed cells (Stempeucel®) at these time points.

TABLE 11

| Sample description | Unprimed sample TSP-2 in ng/ml/ million cells | Primed sample TSP-2 in ng/ml/ million cells |
|---|---|---|
| IMP18-55 48 hr | 4.48 | 1.87 |
| IMP18-55 72 hr | 11.90 | 2.23 |
| IMP18-55 96 hr | 17.87 | 2.52 |
| IMP19-62 48 hr | 7.82 | 2.72 |
| IMP19-62 72 hr | 16.04 | 3.02 |
| IMP19-62 96 hr | 17.25 | 3.10 |
| IMP19-64 48 hr | 3.57 | 2.86 |
| IMP19-64 72 hr | 15.94 | 2.56 |
| IMP19-64 96 hr | 18.26 | 2.56 |
| IMP19-67 48 hr | 11.15 | 4.41 |
| IMP19-67 72 hr | 21.55 | 6.41 |
| IMP19-67 96 hr | 23.79 | 5.37 |
| IMP20-76 48 hr | 16.02 | 7.18 |
| IMP20-76 72 hr | 28.44 | 6.49 |
| IMP20-76 96 hr | 28.88 | 5.78 |
| IMP20-79 48 hr | 11.4 | 6.78 |
| IMP20-79 72 hr | 29.03 | 7.02 |
| IMP20-79 96 hr | 26.80 | 6.54 |
| IMP20-80 48 hr | 13.83 | 5.75 |
| IMP20-80 72 hr | 28.19 | 5.44 |
| IMP20-80 96 hr | 23.42 | 5.17 |
| IMP20-80 48 hr | 9.28 | 4.83 |

TABLE 11-continued

| Sample description | Unprimed sample TSP-2 in ng/ml/ million cells | Primed sample TSP-2 in ng/ml/ million cells |
|---|---|---|
| IMP20-81 72 hr | 30.29 | 5.19 |
| IMP20-81 96 hr | 21.82 | 4.69 |

Conclusion

Stempeucel® primed with the inflammatory cytokines (IFN-γ and TNF-α) reduces the TSP-2 secretion levels compared to the Stempeucel® in unprimed condition.

Example 3—Analysis of TSP-2 and PGE-2 Secretion Potential by Stempeucel® in the Presence and Absence of Inflammatory Cytokines

Objective

To evaluate Stempeucel®'s potential secretion of PGE-2 (anti-inflammatory molecule) during inflammatory environment.

Protocol

Stempeucel® (25 million cells/ml of CS5) from 5 batches were seeded at cell concentration of 1.0 million cells in 10 ml of complete media per T75 flask in duplicate.

One set of cultures were primed with IFN-γ (10 ng/ml) and TNF-α (15 ng/ml) after 24 hrs of seeding and incubated further up to 96 hours from seeding. Another set cultured for 96 hr from seeding without the aforementioned priming was termed as "unprimed".

Condition media samples were collected from both the primed and unprimed set of cultures at 48 hr, 72 hr and 96 hr time point from seeding and analysed for TSP-2, PGE2 and TNF-α ELISA.

Results

The levels of PGE2, TSP-2 and TNF-α were analysed in 5 batches of Stempeucel® in the inflammatory condition and compared to unprimed conditions. The amount of PGE2 secreted by the unprimed samples are comparatively lower than the primed samples (Table 12). The primed samples secrete as much as 24 ng/ml compared to 0.3 ng/ml in unprimed condition (FIG. 2B). There is an inverse correlation observed between PGE2 and TSP-2 secretion, wherein the TSP-2 secretion is higher in unprimed condition compared to primed condition (FIG. 2A). MSCs don't secrete or secrete only negligible amounts of TNF-α in the unprimed conditions. In the priming, wherein IFN-γ and TNF-α were added to the medium, we observed a gradual decrease in the levels of TNF-α with time (FIG. 2C).

TABLE 12

| Sample description | TNF-α levels in ng/ml | | TSP-2 in ng/ml/million cells | | PGE-2 in pg/ml/million cells | |
|---|---|---|---|---|---|---|
| | Unprimed sample | Primed sample | Unprimed sample | Primed sample | Unprimed sample | Unprimed sample |
| IMP19-62 48 hr | 0.00 | 4.46 | 7.82 | 2.72 | 5092.38 | 11392.09 |
| IMP19-62 72 hr | 0.00 | 2.51 | 16.04 | 3.02 | 5075.59 | 11408.97 |
| IMP19-62 96 hr | 0.00 | 2.63 | 17.25 | 3.10 | 4954.73 | 11146.96 |
| IMP19-67 48 hr | 0.00 | 2.20 | 11.15 | 4.41 | 636.16 | 9308.33 |
| IMP19-67 72 hr | 0.00 | 1.96 | 21.55 | 6.41 | 452.55 | 9456.61 |
| IMP19-67 96 hr | 0.00 | 1.29 | 23.79 | 5.37 | 343.61 | 9516.69 |
| IMP20-79 48 hr | 0.00 | 4.16 | 11.4 | 6.78 | 3861.18 | 12365.29 |
| IMP20-79 72 hr | 0.00 | 3.03 | 29.03 | 7.02 | 3456.32 | 23790.14 |
| IMP20-79 96 hr | 0.00 | 2.56 | 26.80 | 6.54 | 2000.86 | 19494.59 |
| IMP20-80 48 hr | 0.00 | 3.93 | 13.83 | 5.75 | 3363.66 | 11324.05 |
| IMP20-80 72 hr | 0.00 | 2.61 | 28.19 | 5.44 | 1676.75 | 11887.47 |
| IMP20-80 96 hr | 0.00 | 2.39 | 23.42 | 5.17 | 658.09 | 13391.89 |
| IMP20-81 48 hr | 0.00 | 3.64 | 9.28 | 4.83 | 4759.15 | 11275.58 |
| IMP20-81 72 hr | 0.00 | 2.96 | 30.29 | 5.19 | 3410.05 | 11864.74 |
| IMP20-81 96 hr | 0.02 | 1.30 | 21.82 | 4.69 | 5086.22 | 11094.73 |

Conclusion

Priming Stempeucel® with the inflammatory cytokines like IFN-γ and TNF-α increases the PGE2 (anti-inflammatory molecule) secretion with simultaneous decrease in TSP-2 secretion levels. Whereas, at unprimed condition PGE2 levels decreased and TSP-2 levels are increased. The data substantiate that Stempeucel® when administered in the knee joint of the OA patient. the inflammatory milieu in the environment will induce the infused Stempeucel® to produce anti-inflammatory molecules like PGE2, which in turn reduce the inflammatory environment and further enhance Stempeucel® to secrete TSP-2.

Additionally, the primed Stempeucel® was also analyzed for chondrogenic differentiation potential and secretion of sGAG. The results showed Chondrocyte differentiated from Stempeucel® primed with inflammatory cytokines (IFN-γ and TNF-α), is capable of inducing the higher expression of proteoglycans i.e. sGAG (which is one of the important building block of cartilage and it accounts for about 3-6% of total cartilage matrix).

The overall schematic representation of the relevance of TSP-2 as a potential indicator for determining the potency of Stempeucel® for OA indication is further provided in FIG. 3.

Example 4—Effect of Hyaluronic Acid on the Performance of MSCs

Objective

To evaluate the effect of hyaluronic acid on performance of MSCs for treating OA.

Protocol

Comparisons were drawn with respect to existing literature studies that employ only mesenchymal stromal cells for osteoarthritis versus the combination of the present disclosure having a composition comprising about 20 to 30 million mesenchymal stromal cells, about 1 ml of multiple electrolyte solution and about 1 ml of protein free, serum free, animal component free formulation of about 2.5% to 5% dimethyl sulfoxide (DMSO); along with about 2 ml of mid molecular weight hyaluronic acid.

All comparisons revealed that the combination of the present disclosure worked much better for treatment of OA and significant improvement was seen in WOMAC Composite Index, Stiffness, Pain levels and WOMAC total score, when compared to a formulation of mesenchymal stromal cells alone, without 2 ml of hyaluronic acid.

The foregoing description of the specific embodiments reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments in this disclosure have been described in terms of preferred embodiments, those skilled in the art will recognize that the embodiments herein can be practiced with modification within the spirit and scope of the embodiments as described herein.

Throughout this specification, the term 'combinations thereof' or 'any combination thereof' or 'any combinations thereof' are used interchangeably and are intended to have the same meaning, as regularly known in the field of patent disclosures.

As regards the embodiments characterized in this specification, it is intended that each embodiment be read independently as well as in combination with another embodiment. For example, in case of an embodiment 1 reciting 3 alternatives A, B and C, an embodiment 2 reciting 3 alternatives D, E and F and an embodiment 3 reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Any discussion of documents, acts, materials, devices, articles and the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

We claim:

1. A method of improving osteoarthritis in a human subject, said method comprising administering to the subject a combination of:

a composition comprising about 20 to 30 million mesenchymal stromal cells, about 1 ml of a multiple electrolyte solution and about 1 ml of protein free, serum free, animal component free formulation of about 2.5% to 5% dimethyl sulfoxide (DMSO); and about 2 ml of mid molecular weight hyaluronic acid, wherein the molecular weight of the mid molecular weight hyaluronic acid is in a range of from about 500,000 Dalton to about 730,000 Dalton, wherein the composition is devoid of human serum albumin (HSA);

wherein the mesenchymal stromal cells are bone marrow derived pooled mesenchymal stromal cells obtained from pooling mesenchymal stromal cells from at least 3 donors; and wherein the administration of the composition or the hyaluronic acid or both, is an ultrasound guided administration, through an intra-articular route.

2. The method as claimed in claim 1, wherein the osteoarthritis is a Grade II or Grade III osteoarthritis.

3. The method as claimed in claim 1, wherein the multiple electrolyte solution comprises sodium chloride, potassium chloride, magnesium chloride hexahydrate, sodium acetate trihydrate, and sodium gluconate.

4. The method as claimed in claim 1, wherein each of the composition and hyaluronic acid are administered through a single intra-articular administration.

5. The method as claimed in claim 1, wherein at least one or both of the composition and hyaluronic acid are administered through an ultrasound guided intra-articular administration.

6. The method as claimed in claim 1, wherein the composition and hyaluronic acid are administered simultaneously or sequentially.

7. The method as claimed in claim 6, wherein the hyaluronic acid is administered post 1 second to 30 minutes of the administration of the composition.

8. The method as claimed in claim 1, wherein the combination provides improvement to the subject in osteoarthritic symptoms selected from a group comprising pain, stiffness and compromised physical function; and improves or maintains quality of cartilage in the subject, in relation to the subject prior to the administration of the said combination.

9. The method as claimed in claim 8, wherein the combination improves mean percentage change from baseline or placebo in at least one of Western Ontario and McMaster Universities Osteoarthritis (WOMAC) composite index score or WOMAC pain index score or WOMAC stiffness index score or WOMAC physical function index score or Visual Analog scale (VAS) score by at least 10% in a span of about 6 months.

10. The method as claimed in claim 8, wherein the combination shows a mean difference in percentage change from baseline or placebo for at least one of WOMAC composite index score or WOMAC pain index score or WOMAC stiffness index score or WOMAC physical function index score or VAS score by at least 15% at the 6 months timepoint.

11. The method as claimed in claim 8, wherein the combination shows a mean difference in percentage change from baseline or placebo for at least one of WOMAC composite index score or WOMAC pain index score or WOMAC stiffness index score or WOMAC physical function index score or VAS score by at least 20% at the 12 months timepoint.

12. The method as claimed in claim 1, wherein the combination increases levels of plasma anti-inflammatory marker interleukin-10 (IL-10) and decreases levels of disease progression urinary marker crosslinked C-telopeptides of type II collagen (CTX-II) in the subject, in relation to the subject prior to the administration of the said combination.

13. The method as claimed in claim 1, wherein the composition comprises 25 million mesenchymal stromal cells.

14. A method of increasing levels of plasma anti-inflammatory marker interleukin-10 (IL-10) and/or decreasing levels of disease progression urinary marker crosslinked C-telopeptides of type II collagen (CTX-II) in a human subject suffering from osteoarthritis, said method comprising administering to the subject a combination of:

a. a composition comprising about 20 to 30 million mesenchymal stromal cells, multiple electrolyte solution and protein free, serum free, animal component free formulation of dimethyl sulfoxide (DMSO); and b. mid molecular weight hyaluronic acid, wherein the molecular weight of the mid molecular weight hyaluronic acid is in a range of from about 500,000 Dalton to about 730,000 Dalton;

wherein the composition is devoid of human serum albumin (HSA);

wherein the mesenchymal stromal cells are bone marrow derived pooled mesenchymal stromal cells obtained from pooling mesenchymal stromal cells from at least 3 donors; and wherein when the combination is administered to the subject, the levels are increased and/or decreased in relation to the subject prior to administration of the said combination.

15. The method as claimed in claim 14, wherein the administration of the composition or the hyaluronic acid or both, is an ultrasound guided administration, through an intra-articular route.

16. The method according to claim 1, wherein an improvement in mean percentage change from baseline when compared to placebo in one or more selected from WOMAC composite index score, WOMAC pain index score, and WOMAC stiffness index score is statistically significant, having a p-value of less than about 0.001 after a treatment period of about 6 months.

17. The method according to claim 14, wherein an improvement in mean percentage change from baseline when compared to placebo in one or more selected from WOMAC composite index score, WOMAC pain index score, and WOMAC stiffness index score is statistically significant, having a p-value of less than about 0.001 after a treatment period of about 6 months.

\* \* \* \* \*